United States Patent
Vardon et al.

(10) Patent No.: US 11,786,886 B2
(45) Date of Patent: Oct. 17, 2023

(54) CATALYSTS AND METHODS FOR THE CONVERSION OF CARBONACEOUS MATERIALS TO LIQUID FUELS

(71) Applicant: Alliance for Sustainable Energy, LLC, Golden, CO (US)

(72) Inventors: Derek Richard Vardon, Lakewood, CO (US); Huong Thi Thanh Nguyen, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 292 days.

(21) Appl. No.: 17/188,334

(22) Filed: Mar. 1, 2021

(65) Prior Publication Data

US 2021/0268483 A1 Sep. 2, 2021

Related U.S. Application Data

(60) Provisional application No. 62/982,129, filed on Feb. 27, 2020.

(51) Int. Cl.
*B01J 23/83* (2006.01)
*B01J 35/10* (2006.01)
(Continued)

(52) U.S. Cl.
CPC .......... *B01J 23/83* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 35/1057* (2013.01); *B01J 35/1061* (2013.01);
(Continued)

(58) Field of Classification Search
CPC ...... B01J 23/83; B01J 23/002; B01J 35/1057; B01J 35/1042; B01J 23/78; B01J 23/80; B01J 35/1066; B01J 35/1019; B01J 35/1047; B01J 35/1014; B01J 35/1061; B01J 23/868; B01J 35/1038; B01J 2523/00; B01J 2523/17; B01J 2523/22; B01J 2523/31; B01J 2523/48; B01J 2523/3712; C10L 1/02; C10L 2200/0469; C07C 29/132

See application file for complete search history.

(56) References Cited

U.S. PATENT DOCUMENTS

2017/0210679 A1* 7/2017 Chojecki ................... C07C 1/12
2018/0215692 A1* 8/2018 Ramasamy ............. C07C 45/45

FOREIGN PATENT DOCUMENTS

WO 2015/148412 A2 10/2015

OTHER PUBLICATIONS

Abbadi et al., "Study on Solid Acid Catalyzed Hydrolysis of Maltose and Related Polysaccharides", Starch, 1998, vol. 50, No. 1, pp. 23-28.
(Continued)

*Primary Examiner* — Vishal V Vasisth
(74) *Attorney, Agent, or Firm* — Michael A. McIntyre

(57) ABSTRACT

The present disclosure relates to a composition that includes copper (Cu), aluminum (Al), oxygen, and an element (M) that includes at least one of magnesium, cerium, and/or a transition metal, where the copper and the element are present at a first molar ratio relative to the aluminum between about 0.1:1 and about 30:1 ((Cu+M):Al), and the copper and the element are present at a second molar ratio between about 0.1:4 and about 20:1 (Cu:M).

19 Claims, 40 Drawing Sheets

(51) Int. Cl.
C07C 29/132 (2006.01)
C10L 1/02 (2006.01)
(52) U.S. Cl.
CPC ......... B01J 35/1066 (2013.01); C07C 29/132 (2013.01); C10L 1/02 (2013.01); C10L 2200/0469 (2013.01)

(56) References Cited

OTHER PUBLICATIONS

Abu-Omar et al., "Guidelines for performing lignin-first biorefining", Energy & Environmental Science, 2021, vol. 14, pp. 262-292.
Anderson et al., "Reductive Catalytic Fractionation of Corn Stover Lignin", ACS Sustainable Chemistry & Engineering, 2016, vol. 4 No. 12, pp. 6940-6950.
Anderson et al., "Engineering, Kinetic studies of lignin solvolysis and reduction by reductive catalytic fractionation decoupled in flow-through reactors", ACS Sustainable Chemistry & Engineering, 2018, vol. 6, No. 6, pp. 7951-7959.
Barta et al., "Catalytic Conversion of Nonfood Woody Biomass Solids to Organic Liquids", Accounts of Chemical Research, 2014, vol. 47, No. 5, pp. 1503-1512.
Behrens et al., "The active site of methanol synthesis over Cu/ZnO/Al2O3 industrial catalysts", Science, May 2012, vol. 336, No. 6083, pp. 893-897.
Chupka et al., "Heat of vaporization measurements for ethanol blends up to 50 volume percent in several hydrocarbon blendstocks and implications for knock in SI engines", SAE International Journal of Fuels and Lubricants, Apr. 2015, vol. 8, No. 2, pp. 251-263.
De Vrieze et al., "Role of surface hydroxyl species in copper-catalyzed hydrogenation of ketones", ACS Catalysis, Jul. 2018, vol. 8, No. 8, pp. 7539-7548.
Dhepe et al., "Hydrolysis of sugars catalyzed by water-tolerant sulfonated mesoporous silicas", Catalysis Letters, 2005, vol. 102, Nos. 3-4, pp. 163-169.
Ershov et al., "Characteristics of isohexene as a novel promising high-octane gasoline booster", Energy & Fuels, 2020, vol. 34, No. 7, pp. 8139-8149.
Fioroni et al., "Measurement of heat of vaporization for research gasolines and ethanol blends by DSC/TGA", Energy & Fuels, 2018, vol. 32, No. 12, pp. 12607-1261.
Fisher et al., "A Mechanistic Study of Methanol Decomposition over Cu/SiO2, ZrO2/SiO2, and Cu/ZrO2/SiO2", Journal of Catalysis, 1999, vol. 184, No. 2, pp. 357-376.
Galebach et al., "Production of Alcohols from Cellulose by Supercritical Methanol Depolymerization and Hydrodeoxygenation", ACS Sustainable Chemistry & Engineering, 2018, vol. 6, pp. 4330-4344.
Galebach et al., "Supercritical Methanol Depolymerization and Hydrodeoxygenation of Maple Wood and Biomass- Derived Oxygenates into Renewable Alcohols in a Continuous Flow Reactor", ACS Sustainable Chemistry & Engineering, 2019, vol. 7, No. 18, pp. 15361-15372.
Galebach et al., "Production of renewable alcohols from maple wood using supercritical methanol hydrodeoxygenation in a semi-continuous flowthrough reactor", Green Chemistry, 2020, vol. 22, No. 23, pp. 8462-8477.
Gaspar et al., "Top Ten Blendstocks Derived From Biomass For Turbocharged Spark Ignition Engines: Bio-blendstocks With Potential for Highest Engine Efficiency", Technical Report PNNL-28713, Sep. 2019, pp. 1-138.
Ginés et al. "Activity and structure-sensitivity of the water-gas shift reaction over CuZnAl mixed oxide catalysts", Applied Catalysis A: General, Oct. 1995, vol. 131, No. 2, pp. 283-296.
Helali et al., "Scaling reducibility of metal oxides", Theoretical Chemistry Accounts: Theory, Computation, and Modeling, Springer Verlag, 2017, vol. 136, No. 9, pp. 1-49.
Hu et al., "Hydrogenation of biomass-derived compounds containing a carbonyl group over a copper-based nanocatalyst: Insight into the origin and influence of surface oxygen vacancies", Journal of Catalysis 2016, 340, 184-195.
Kattel et al., "Active sites for CO2 hydrogenation to methanol on Cu/ZnO catalysts", Science, Mar. 2017, vol. 355, No. 6331, pp. 1296-1299.
Konsolakis et al., "The role of Copper-Ceria interactions in catalysis science: Recent theoretical and experimental advances", Applied Catalysis B: Environmental, Dec. 2016, vol. 198, pp. 49-66.
Kumaniaev et al., "Lignin depolymerization to monophenolic compounds in a flow-through system", Green Chemistry, 2017, vol. 19, No. 24, pp. 5767-5771.
Li et al., "Renewable High-Octane Gasoline by Aqueous-Phase Hydrodeoxygenation of C5 and C6 Carbohydrates over Pt/Zirconium Phosphate Catalysts", 2010, vol. 3, No. 10, pp. 1154-1157.
Li et al., "Kinetic and mechanistic insights into hydrogenolysis of lignin to monomers in a continuous flow reactor", Green Chemistry, 2019, vol. 21, No. 13, pp. 3561-3572.
Li et al., "Aqueous-phase hydrodeoxygenation of sorbitol with Pt/SiO2—Al2O3: Identification of reaction intermediates", Journal of Catalysis, Mar. 2010, vol. 270, No. 1, pp. 48-59.
Liu et al., "Ce modified Cu/Zn/Al catalysts for direct liquefaction of microcrystalline cellulose in supercritical methanol", Cellulose, 2019, vol. 26, pp. 8291-8300.
Luterbacher et al., "Targeted chemical upgrading of lignocellulosic biomass to platform molecules", Green Chemistry, 2014, vol. 16, No. 12, pp. 4816-4838.
McClelland et al., "Supercritical methanol depolymerization and hydrodeoxygenation of lignin and biomass over reduced copper porous metal oxides", 2019, Green Chemistry, vol. 21, No. 11, pp. 2988-3005.
Macala et al., "Materials, Hydrogen transfer from supercritical methanol over a solid base catalyst: A model for lignin depolymerization", ChemSusChem, 2009, vol. 2, No. 3, pp. 215-217.
Matson et al., "One-Pot Catalytic Conversion of Cellulose and of Woody Biomass Solids to Liquid Fuels", Journal of the American Chemical Society, 2011, vol. 133, pp. 14090-14097.
Murcia-Mascarós et al., "Oxidative Methanol Reforming Reactions on CuZnAl Catalysts Derived from Hydrotalcite-like Precursors", 2001, vol. 198, No. 2, pp. 338-347.
Renders et al., "Lignin-first biomass fractionation: the advent of active stabilisation strategies", Energy & Environmental Science, 2017, vol. 10 No. 7, pp. 1551-1557.
Rinaldi et al., "Depolymerization of Cellulose Using Solid Catalysts in Ionic Liquids", Angewandte Chemie, 2008, vol. 47, No. 42, pp. 8047-8050.
San et al., "New Synthesis Method of Ethanol from Dimethyl Ether with a Synergic Effect between the Zeolite Catalyst and Metallic Catalyst", Energy & Fuels 2009, vol. 23, No. 5, pp. 2843-2844.
Sanna et al., "Hydrodeoxygenation of the aqueous fraction of bio-oil with Ru/C and Pt/C catalysts", Apr. 2015, Applied Catalysis B: Environmental, vol. 165, pp. 446-456.
Sharma et al., "Selective hydrogenolysis of glycerol to propylene glycol by using Cu: Zn: Cr: Zr mixed metal oxides catalyst", Applied Catalysis A; General, May 2014, vol. 477, pp. 147-156.
Shrotri et al., "Cellulose Depolymerization over Heterogeneous Catalysts", Accounts of Chemical Research, 2018, vol. 51, No. 3, pp. 761-768.
Sun et al., "Complete lignocellulose conversion with integrated catalyst recycling yielding valuable aromatics and fuels", Nature Catalysis, Jan. 2018, vol. 1, pp. 82-92.
Twigg et al., "Deactivation of supported copper metal catalysts for hydrogenation reactions", Applied Catalysis A: General, Apr. 2001, vol. 212, Nos. 1-2, pp. 161-174.
Twigg et al., "Deactivation of copper metal catalysts for methanol decomposition, methanol steam reforming and methanol synthesis", 2003, 22 (3-4), 191-203.
Valle et al., "Comparative study of biodiesel oxidation stability using Rancimat, PetroOXY, and low P-DSC", Journal of Thermal Analysis and Calorimetry, 2014, vol. 116, No. 1, pp. 113-118.

(56) References Cited

OTHER PUBLICATIONS

Wang et al., "Insight into the Balancing Effect of Active Cu Species for Hydrogenation of Carbon-Oxygen Bonds", ACS Catalysis, 2015, vol. 5, No. 10, pp. 6200-6208.

Wu et al., "Hydrogenolysis of cellulose toC4-C7alcohols over bi-functional CuO—MO/Al2O3 (M=Ce,Mg,Mn,Ni,Zn) catalysts coupled with methanol reforming reaction", Bioresource Technology, 2013, vol. 137, pp. 311-317.

Xiao et al., "Synergetic effect between Cu0 and Cu+ in the Cu—Cr catalysts for hydrogenolysis of glycerol", Catalysis Today, Oct. 2014, vol. 234, pp. 200-207.

Yao et al., "Unraveling the dynamic nature of a CuO/CeO2 catalyst for CO oxidation in operando: a combined study of XANES (fluorescence) and Drifts", ACS Catalysis, Apr. 2014, vol. 4, No. 6, pp. 1650-1661.

Yong et al., "Review of methanol reforming-Cu-based catalysts, surface reaction mechanisms, and reaction schemes", 2013, vol. 38, No. 22, pp. 9541-9552.

Renders et al., "Reductive catalytic fractionation: state of the art of the lignin-first biorefinery", Current Opinion in Biotechnology, 2019, vol. 56, pp. 193-201.

\* cited by examiner

CATALYSTS AND METHODS FOR THE CONVERSION OF CARBONACEOUS MATERIALS TO LIQUID FUELS

CROSS-REFERENCE TO RELATED APPLICATIONS

This application claims priority from U.S. Provisional Patent Application No. 62/982,129 filed on Feb. 27, 2020, the contents of which are incorporated herein by reference in its entirety.

CONTRACTUAL ORIGIN

This invention was made with government support under Contract No. DE-AC36-08GO28308 awarded by the Department of Energy. The government has certain rights in the invention.

BACKGROUND

Tandem solvolytic (i.e., solvent processing for chemical bond cleavage and chemical bond formation with solubilization) and catalytic conversion of biomass in supercritical methanol to liquid fuels has recently emerged as a promising biomass valorization technology with an exceptionally high carbon balance. The process takes advantage of supercritical methanol to depolymerize biomass, and of $H_2$ generated from methanol reforming as a reducing agent for the hydrodeoxygenation of sugar oligomers to C2-C6 mixed oxygenates with up to 70% selectivity to aliphatic (i.e. non-aromatic) alcohols. Multifunctional mixed oxide-supported copper has been demonstrated to be an active catalyst for aliphatic alcohol production. However, copper-based catalysts can suffer from deactivation, predominantly by thermal sintering. Thus, there remains a need for better performing catalysts for the catalytic conversion of biomass and other carbonaceous materials to alcohols and fuels.

SUMMARY

An aspect of the present disclosure is a composition that includes copper (Cu), aluminum (Al), oxygen, and an element (M) that includes at least one of magnesium, cerium, and/or a transition metal, where the copper and the element are present at a first molar ratio relative to the aluminum between about 0.1:1 and about 30:1 ((Cu+M):Al), and the copper and the element are present at a second molar ratio between about 0.1:4 and about 20:1 (Cu:M). In some embodiments of the present disclosure, the second molar ratio may be between about 1:1 and about 10:4 (Cu:M). In some embodiments of the present disclosure, the copper, aluminum, and the M are each incorporated into an oxide. In some embodiments of the present disclosure, the transition metal may be at least one of zinc, zirconium, chromium, scandium, titanium, niobium, vanadium, hafnium, tungsten, and/or tantalum. In some embodiments of the present disclosure, M may include at least one of magnesium, zirconium, cesium, and/or zinc.

In some embodiments of the present disclosure, the composition may further include a third molar ratio of a molar hydrogen ($H_2$) capacity, in moles of $H_2$ per gram of the composition ($c_1$), to a molar concentration of the Cu, in moles of Cu per gram of the composition ($c_2$), where the third molar ratio may be between about 0.5:1 and about 10:1 ($c_1$:$c_2$). In some embodiments of the present disclosure, the third molar ratio may be between about 1:1 and about 3.4:1.

In some embodiments of the present disclosure, the composition may further include an average pore size between about 0.1 nm and about 60 nm. In some embodiments of the present disclosure, the average pore size is between about 1.0 nm and about 10 nm.

In some embodiments of the present disclosure, the composition may further include a pore volume between about 0.1 cm$^3$/g and about 30 cm$^3$/g. In some embodiments of the present disclosure, the pore volume may be between about 0.1 cm$^3$/g and about 1.6 cm$^3$/g. In some embodiments of the present disclosure, the composition may further include an acid site density between about 50 μmol acid sites/g composition (μmol/g) and about 350 μmol/g. In some embodiments of the present disclosure, the acid site density may be between about 125 μmol/g and about 300 μmol/g.

In some embodiments of the present disclosure, the composition may further include a surface area between about 50 m$^2$/g and about 500 m$^2$/g. In some embodiments of the present disclosure, the surface area may be between about 140 m$^2$/g and about 265 m$^2$/g. In some embodiments of the present disclosure, the composition may further include a basic site density between about 1.0 μmol basic sites/g composition (μmol/g) and about 200 μmol/g. In some embodiments of the present disclosure, the basic site density may be between about 25 μmol/g and about 150 μmol/g.

An aspect of the present disclosure is a method that includes contacting a feedstock that includes at least one of a biomass and/or a non-biomass carbonaceous material with a composition and supercritical methanol, where the contacting converts at least a portion of the feedstock to a mixture that includes an alcohol. The composition includes copper (Cu), aluminum (Al), oxygen, and an element (M) including at least one of magnesium, cerium, or a transition metal, where the copper and the element are present at a first molar ratio relative to the aluminum between about 0.1:1 and about 30:1 ((Cu+M):Al), and the copper and the element are present at a second molar ratio between about 0.1:4 and about 20:1 (Cu:M).

An aspect of the present disclosure is a fuel composition that includes at least one of 2-methyl-1-propanol, ethanol, 1-propanol, 2-propanol, 2-butanol, iso-butanol, 1-butanol, 3-methyl-2-butanol, 2-methyl-2-pentanol, 1-pentanol, and/or 3-hexanol. In some embodiments of the present disclosure, the fuel composition may further include at least one of methyl acetate, 2-methyl furan, methyl propionate, methyl butyrate, 3-hexanone, 2-methyl(methyl butanoate), 1,2-butanediol, methyl pentanoate, and/or 2-methylcyclopentanone.

BRIEF DESCRIPTION OF THE DRAWINGS

Some embodiments are illustrated in referenced figures of the drawings. It is intended that the embodiments and figures disclosed herein are to be considered illustrative rather than limiting.

DETAILED DESCRIPTION

Figure 1:
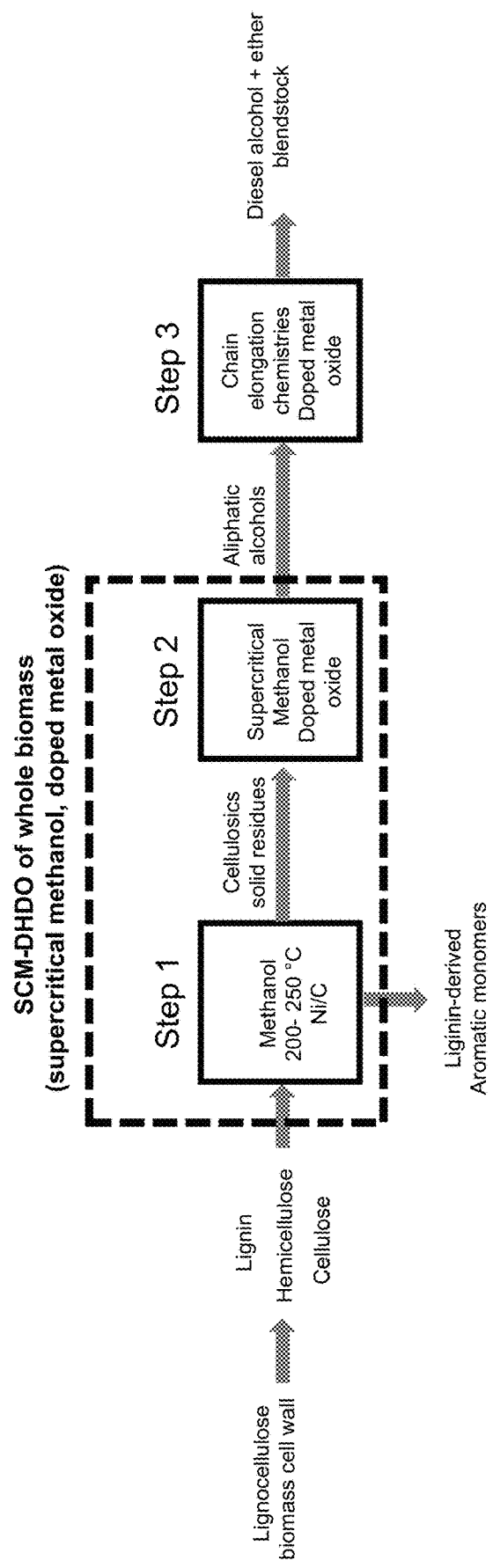
FIG. 1 illustrates scheme to convert lignocellulose biomass to diesel blendstock, according to some embodiments of the present disclosure.

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to material designs that enhance catalyst activity and stability. Catalysts are described herein having, among other things, a thermally stable metal and/or a highly reducible mixed oxide support, resulting in increased reactivity and extended catalyst lifetimes. As shown herein, hydrodeoxygenation metallic catalysts with higher cohesive energies than copper, including nickel, cobalt, and palladium, are more thermally stable and withstand higher operating temperatures (≥about 300° C.). Also shown herein, reducible metal oxide catalyst supports with active surface oxygen abundancy can potentially increase the alcohol production rate by promoting methanol reforming. In addition, the composition of metals and/or supports can dictate catalyst physiochemical properties, metal particle size, and species, hence its activity and durability. Moreover, fuel values and the corresponding optimal composition of the oxygenate products may be targeted using at least some of the compositions described herein. Thus, the present disclosure relates to, among other things, metallic catalysts supported on reducible mixed oxides that can improve the production rate, selectivity, and time-on-stream stability for the solvolysis and catalysis of cellulosic biomass to C2-C6 aliphatic alcohols. Furthermore, it is shown herein how desirable oxygenate mixtures may be achieved through the tuning of such catalysts and/or changing the process operating conditions, resulting in liquid fuels having optimal fuel properties.

As described below, a two step-reaction combining a first lignin treating/removal step followed by a subsequent step for the catalytic conversion of the residual cellulosic materials is capable of converting biomass to alcohols. Here, lignin is first extracted from biomass and selectively valorized to aromatic monomers under reductive catalytic fractionation at mild temperature (200-250° C.) in methanol solvent (See FIG. 1, Step 1). Subsequently, the cellulosic residues (e.g., cellulose and/or hemicellulose) may be fully converted, catalytically, with up to 68% selectivity for aliphatic alcohols under supercritical methanol and copper-doped mixed oxide catalyst conditions (see FIG. 1, Step 2). Therefore, the complete valorization of woody biomass to oxygenated liquids via supercritical methanolysis coupled with catalytic hydrodeoxygenation (SCM-DHDO) is promising because it offers the advantages of (1) one-pot conversion of raw biomass to high hydrogen-to-carbon ratio chemical building blocks, (2) the utilization of solid catalysts synthesized using Earth abundant metals, (3) the utilization of an inexpensive hydrogen donor solvent, and (4) the ability to utilize varied feedstocks without expensive pretreatments. In the SCM-DHDO process (see FIG. 1, dashed box), woody biomass may be solvolyzed in methanol at supercritical condition (for example at about 300° C. and about 2000 psig), followed by catalytic hydrodeoxygenation by a mixed metal oxide catalyst to liquid alcohols. As described herein, the resultant alcohol product mixtures may be subsequently functionalized to diesel-graded blend-stock by chain elongation chemistries (see FIG. 1, Step 3).

Thus, as described herein, higher yields of aliphatic alcohols may be achieved by tuning the redox properties, acid-base density, and/or porosity in multifunctional metal-doped metal oxides catalysts. In addition, catalyst stability studies were conducted to investigate the effect of biomass impurities on catalyst lifetimes. Furthermore, it is demonstrated herein how desirable oxygenate mixture compositions for liquid fuel applications may be targeted through tuning the catalyst design and/or the process operating conditions.

Effect of reducibility of support oxide: Direct catalytic conversion of cellulosics (Step 2 of FIG. 1) to aliphatic alcohols may occur via supercritical methanolysis to sugar-derived oligomers and catalytic upgrading of the oligomers to the aliphatic alcohols. Major reaction steps likely include one or more of cellulosics depolymerization, sugar retro aldol condensation (i.e., reaction in which a beta-hydroxy carbonyl compound decomposes into an aldehyde or ketone, plus another carbonyl compound), light oxygenate hydrodeoxygenation (HDO), and/or methanol reforming, as shown in FIG. 2. The complex reaction network may require multifunctional catalysts (i.e., catalyst that contain more than one functionality that facilitate acidic, basic, reductive, and/or oxidative chemistry). While depolymerization and retro aldol are generally catalyzed by acid/base catalysts, HDO and methanol reforming typically require metal sites.

Among the proposed reaction steps, hydrodeoxygenation of light oxygenates affects the final yield of the aliphatic alcohol products. Hydrodeoxygenation needs hydrogen gas as a reducing agent, which may form via methanol reforming. Therefore, increasing methanol reforming activity may be a catalyst design strategy to improve aliphatic alcohol yields. Mixed metal oxide catalysts containing copper may synergistically facilitate methanol decomposition. Specifically, the oxide portion of the catalyst may provide a surface oxygen source for adsorbed carbon species, while copper and/or other metal sites may facilitate $H_2$ removal (referred to herein as "hydrogen spillover"). Therefore, metal oxide catalysts with higher active surface oxygen storage capacity (to create more oxygen vacancy) may increase methanol reforming activity and, as a result, aliphatic alcohol production rate. Thus, as defined herein, a copper-containing mixed metal oxide catalyst is represented by $CuMAlO_x$, where M is a metal with examples including magnesium, cerium, zirconium, and/or zinc. Further, each of the copper, aluminum, and/or M are covalently incorporated into the oxide. This is shown schematically in Scheme 1 below:

Scheme 1

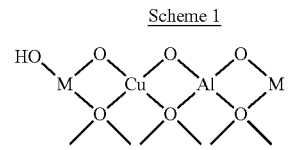

So, as shown in Scheme 1, a mixed metal oxide catalyst may contain two or more metals, in this case at least three metals, incorporated covalently into an oxide structure. Therefore, in some embodiments of the present disclosure, each of the metal (e.g., M, Cu, and/or Al) may be present at both the outer surface of the catalyst and present within the internal mass of the catalyst. As described herein, a mixed metal oxide catalyst may be in a solid form, including as a powder and/or granulated form having a characteristic length (e.g., diameter) between about 10 microns and about 3 mm, or between about 10 microns and about 500 microns (e.g., for powders).

Thus, as described herein, the notation $CuMAlO_x$ does not mean the copper, M, and aluminum are present in a stoichiometric ration of 1:1:1. Further, x in the $O_x$, does not indicate a specific range of the stoichiometry for oxygen; instead, $O_x$ simply indicates that each of copper, M, and aluminum are present as oxides in the composition, as shown above in Scheme 1. In other words, $CuMAlO_x$ is shorthand notation for $(CuO)_a(MgO)_b(Al2O3)_c$ where the a:b:c is the ratio of Cu:Mg:Al, as described in more detail below.

Figure 3:
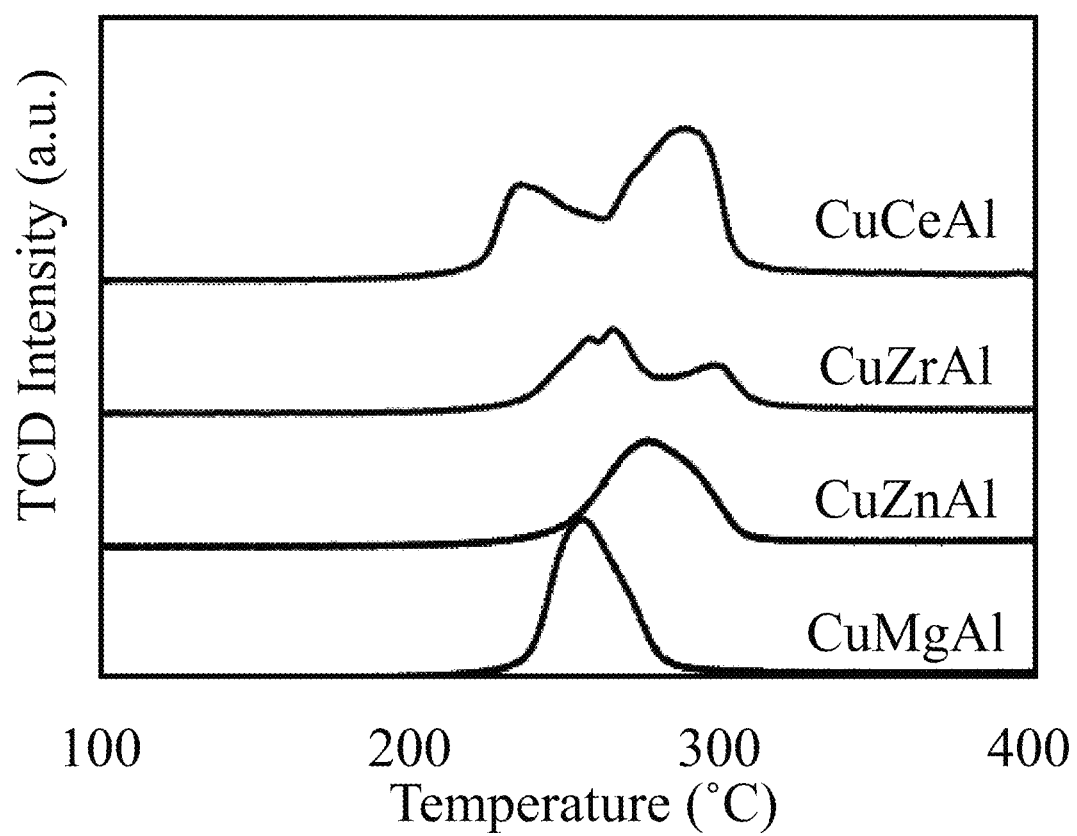
FIG. 3 illustrates a temperature programmed reduction (TPR) profile of Cu-based oxide catalysts, according to some embodiments of the present disclosure.

As described herein, various copper-containing mixed metal oxide catalysts were synthesized, characterized, and tested for direct catalytic conversion of delignified hybrid poplar in batch reactions performed at about 300° C. To determine the reducibility of the copper-based mixed oxide catalysts, $H_2$ temperature programmed reduction (TPR) was measured to determine the total $H_2$ consumption. While the amount of $H_2$ consumed was comparable with copper content for $CuMgAlO_x$ catalyst it is in excess for all other tested Cu-based catalysts, especially for $CuCeAlO_x$ ($H_2$/Cu molar ratio ~3.41), likely due to $H_2$ spillover and oxygen vacancy generation (see Table 1). Reduction temperatures were also significantly lower for $CuZrAlO_x$ ($T_{min}$=200° C.) and $CuCeAlO_x$ ($T_{min}$=175° C.) than for $CuMgAlO_x$ (($T_{min}$=255° C.) as shown in FIG. 3. The $H_2$ TPR results confirmed that unlike the nonreducible MgAlO$_x$ support, other oxide supports have higher reducibility and oxygen storage capacity. The total oxygen storage capacity is evaluated as a descriptor for methanol reforming activity and alcohol yield production. H$_2$ TPR consumption is a measure of the catalyst's ability utilize hydrogen, which can correlate to how well the catalyst reduces organic compounds when reacted with hydrogen. H$_2$ TPR consumption can be a function of both the metal Cu sites and the metal oxide supports.

TABLE 1

H$_2$ TPR Consumption of Copper-based Oxides.

| Catalyst | Cu ICP content (μmol/g) | H$_2$ TPR consumption (μmol/g) | H$_2$/Cu |
|---|---|---|---|
| CuCeAl | 939 | 3205 | 3.41 |
| CuZnAl | 1626 | 2355 | 1.45 |
| CuZnAl | 2045 | 2522 | 1.24 |
| CuMgAl | 2832 | 2820 | 0.99 |

Figure 4:
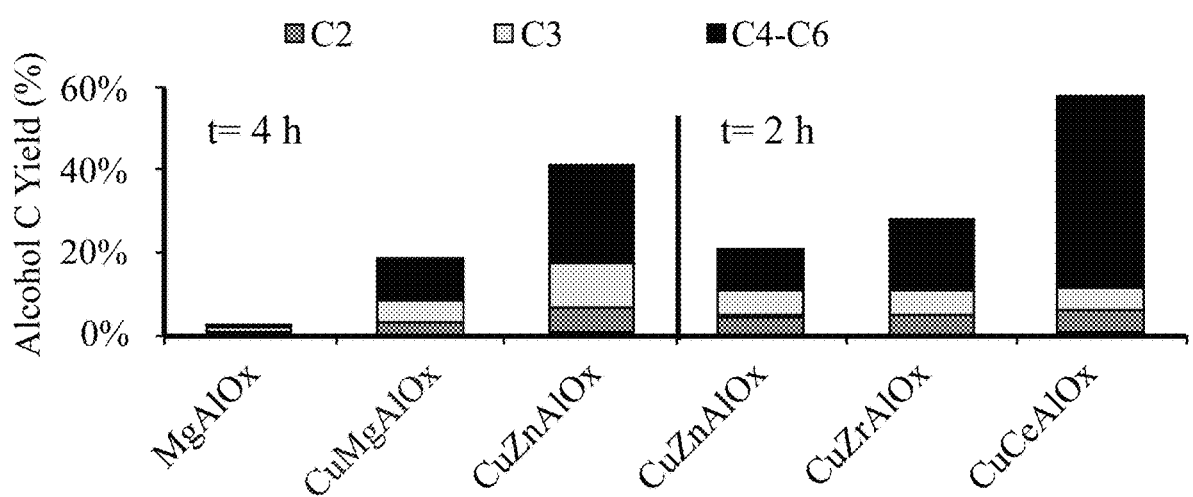
FIG. 4 illustrates alcohol yield obtained from various Cu-based mixed oxides from experiments corresponding to Step 2 of FIG. 1, according to some embodiments of the present disclosure. Reaction conditions: batch, 1 g delignified hybrid poplar, reduced mixed oxide catalyst, 30 mL methanol, 300° C., biomass carbon:redox metal=63:1 (mol basis).
Figure 5:
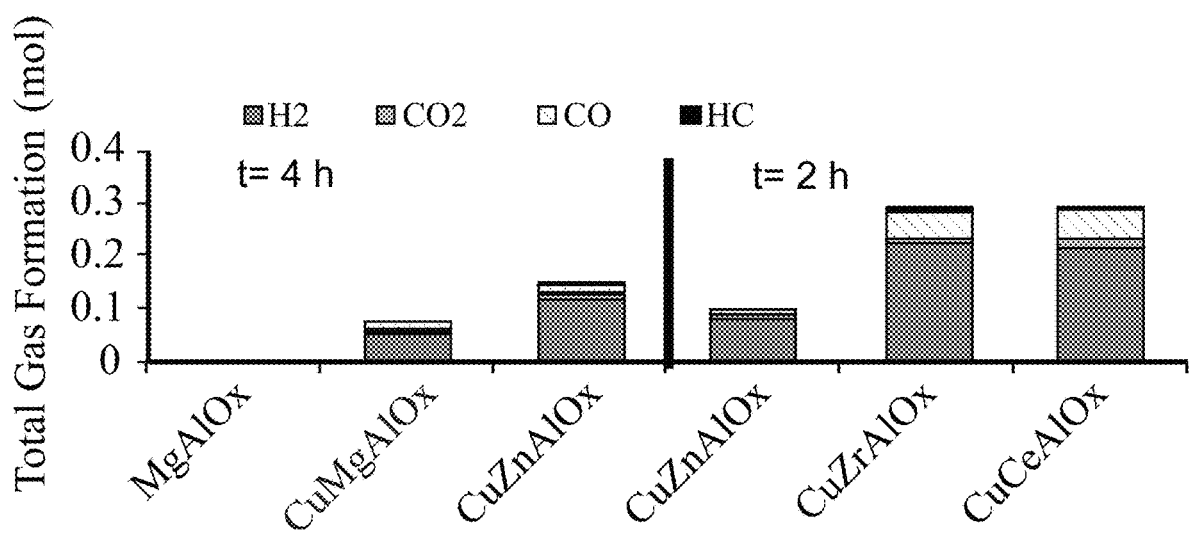
FIG. 5 illustrates gas formation obtained from various Cu-based mixed oxides from experiments corresponding to Step 2 of FIG. 1, according to some embodiments of the present disclosure. Reaction conditions: batch, 1 g delignified hybrid poplar, reduced mixed oxide catalyst, 30 mL methanol, 300° C., biomass carbon:redox metal=63:1 (mol basis).

C2-C6 aliphatic alcohol yields and gas production from methanol reforming by various Cu-based mixed oxide catalysts are shown in FIG. 4 and FIG. 5, respectively. Little alcohol and H$_2$ were produced in the absence of Cu, indicating the critical role of the redox metal for hydrodeoxygenation and methanol reforming. Total alcohol yield significantly increased from 18% CuMgAlO$_x$ to 42% for CuZnAlO$_x$ after about 4 hours of reaction and to 58% for CuCeAlO$_x$ after only about 2 hours of reaction time. In addition, selectivity to C4-C6 alcohols also improved when Mg was replaced by Zn, Zr and Ce in the material makeup. H$_2$ formation from methanol reforming also increased in the order of CuMgAl<CuZnAl<CuZrAl~CuCeAl. Higher H$_2$ and alcohol yield of the copper-based oxide correlates with the higher H$_2$ TPR/Cu ratio, supporting the hypothesis that oxygen storage capacity of the support oxide is an important design factor that influences catalyst activity. These finding may offer opportunities for process improvements that also improve process economics. Enhanced catalyst activity may help to lower operating temperature and pressure, which may in turn reduce the intensive energy demand of the supercritical methanol condition. Higher selectivity to fuel application targeted C4-C6 alcohols by a more reducible oxide support potentially offers lower distillation costs, where distillation separates and provides the recycle of lighter alcohols and methanol. In addition, while metal-catalyzed chemistries usually employ costly and precious metal (e.g., Pt, Pd, Ru) for enhanced activity and selectivity, the catalysts described herein utilize a reducible oxide support while maintaining cheap and abundant copper as the active metal can significantly reduce catalyst cost.

Figure 6:
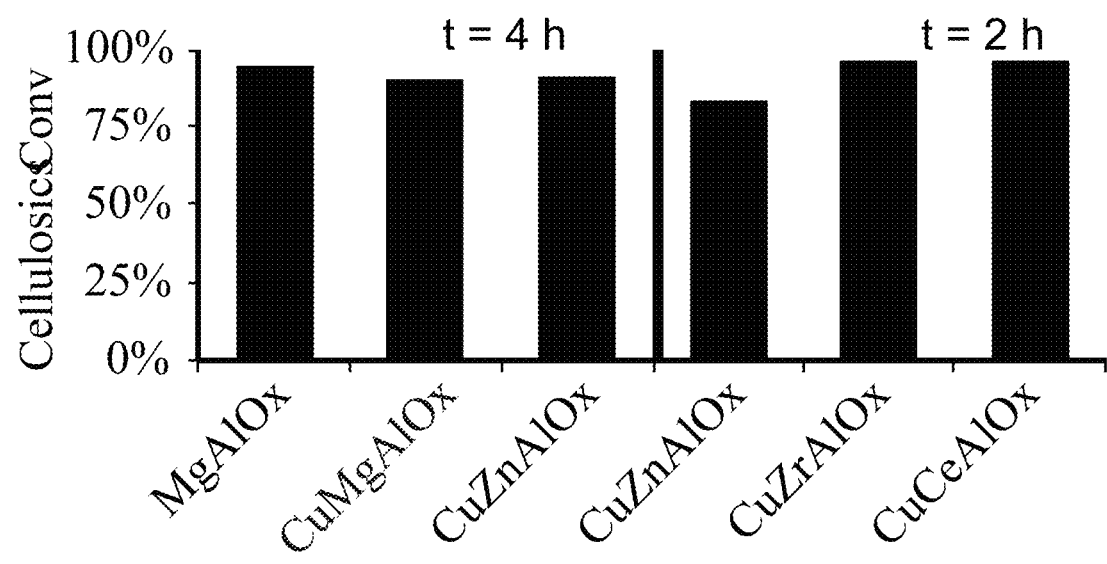
FIG. 6 illustrates cellulosic conversion obtained from various Cu-based oxide catalysts with delignified hybrid poplar or sorbitol as the feedstock, according to some embodiments of the present disclosure. Reaction condition: batch, 1 g delignified hybrid poplar (or 1.2 g sorbitol), reduced mixed oxide catalyst, 30 mL methanol, 300° C., 2 h, biomass (sorbitol) carbon:Cu=63:1 (mol basis).

Effect of catalyst porosity, acidity, and/or basicity: Beside methanol reforming and hydrodeoxygenation of light oxygenates, depolymerization of biomass and its derived sugar oligomers is also important for C2-C6 alcohol production. Biomass solvolysis appears to be facilitated by thermal energy and acidity of supercritical methanol and with minimal contribution from the catalyst (see FIG. 6). The marginal catalytic effect is probably due to limited solid-solid interaction of biomass and catalyst. However, depolymerization and retro-aldol reactions of methanol-solubilized sugar oligomers may be enhanced by providing more accessible catalyst acid sites and/or basic sites. Since, the average diameter of oligosaccharides can be up to hundreds of nanometers depending on the degree of polymerization (dp), diffusion of the sugar molecules to the internal acid/base catalytic site can be a limiting factor. Therefore, catalyst design strategies should consider pore structure.

Figure 7:
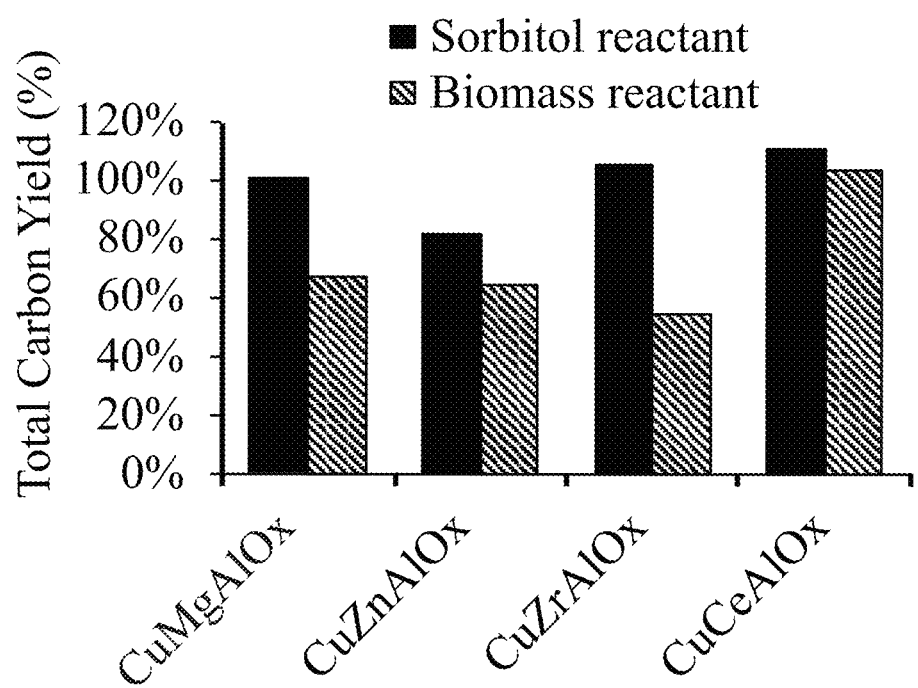
FIG. 7 illustrates total GC carbon yield obtained from various Cu-based oxide catalysts with delignified hybrid poplar or sorbitol as the feedstock, according to some embodiments of the present disclosure. Reaction condition: batch, 1 g delignified hybrid poplar (or 1.2 g sorbitol), reduced mixed oxide catalyst, 30 mL methanol, 300° C., 2 h, biomass (sorbitol) carbon:Cu=63:1 (mol basis).
Figure 8:
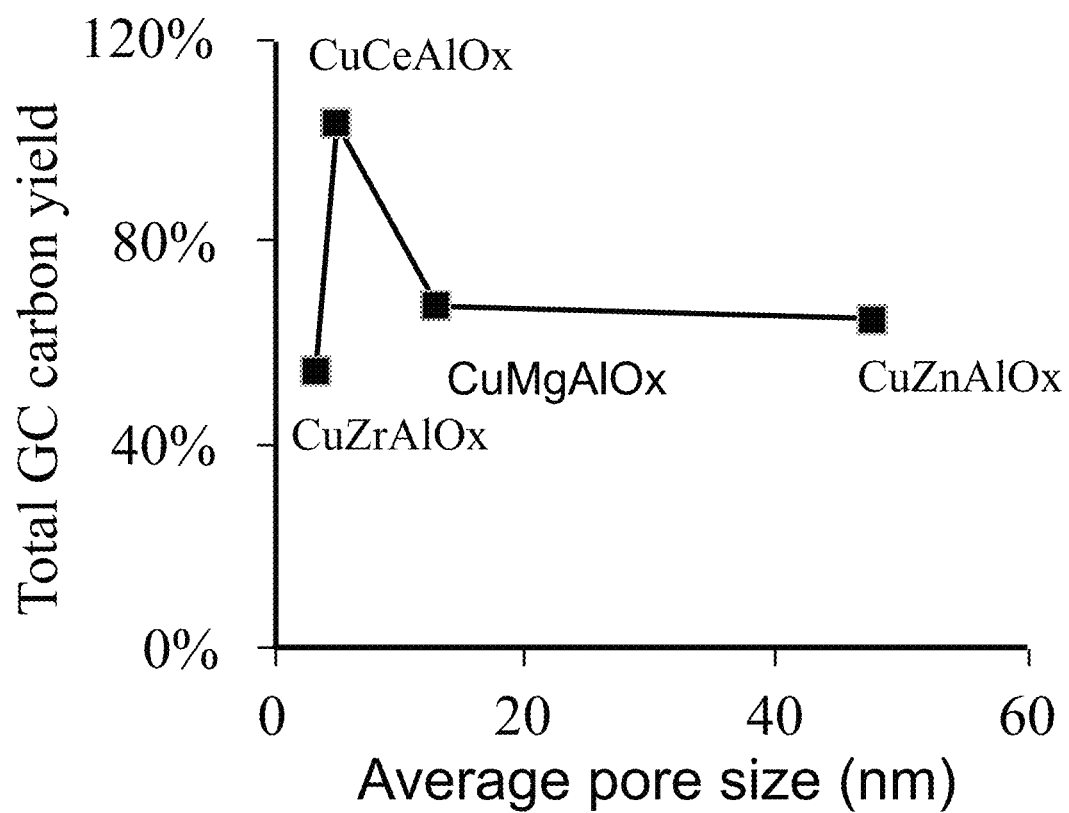
FIG. 8 illustrates the correlation to the catalyst's average pore size with delignified hybrid poplar as the feedstock, according to some embodiments of the present disclosure. Reaction condition: batch, 1 g delignified hybrid poplar (or 1.2 g sorbitol), reduced mixed oxide catalyst, 30 mL methanol, 300° C., 2 h, biomass (sorbitol) carbon:Cu=63:1 (mol basis).
Figure 9:
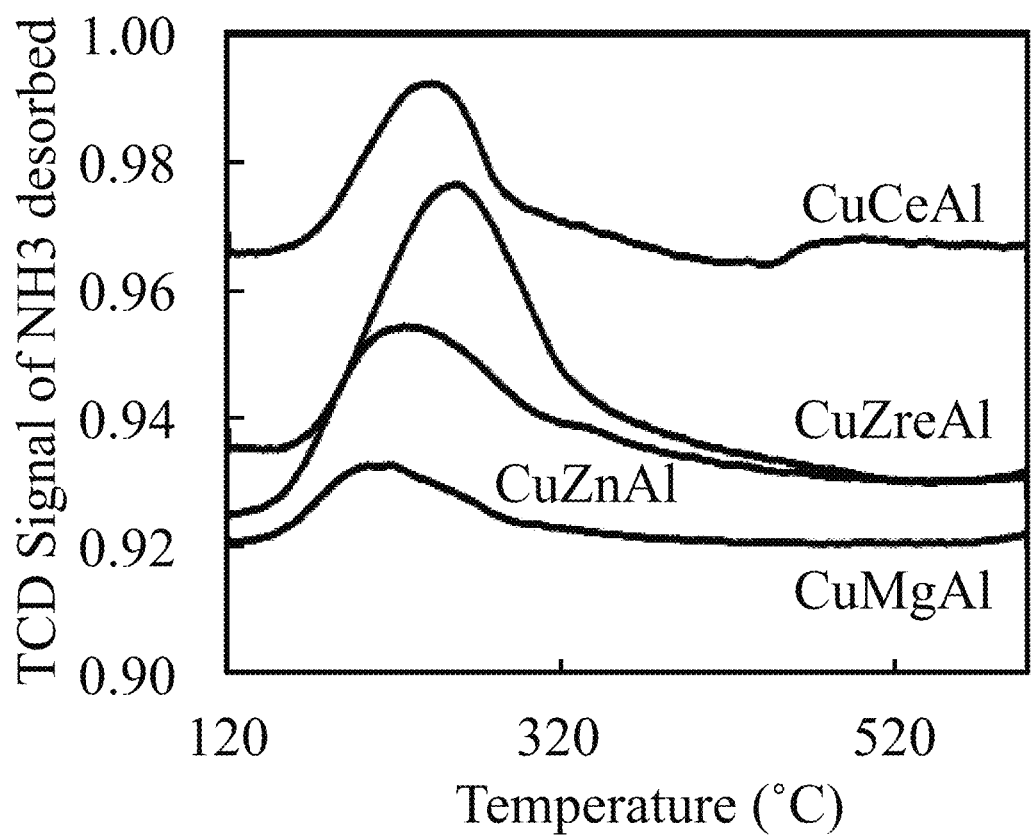
FIG. 9 illustrates $NH_3$ TPD profile of Cu-based mixed oxide catalysts, according to some embodiments of the present disclosure. Reaction condition: Reaction condition: batch, 1.2 g sorbitol, reduced mixed oxide catalyst, 30 mL methanol, 300° C., 2 h, sorbitol carbon:Cu=63:1 (mol basis).
Figure 10:
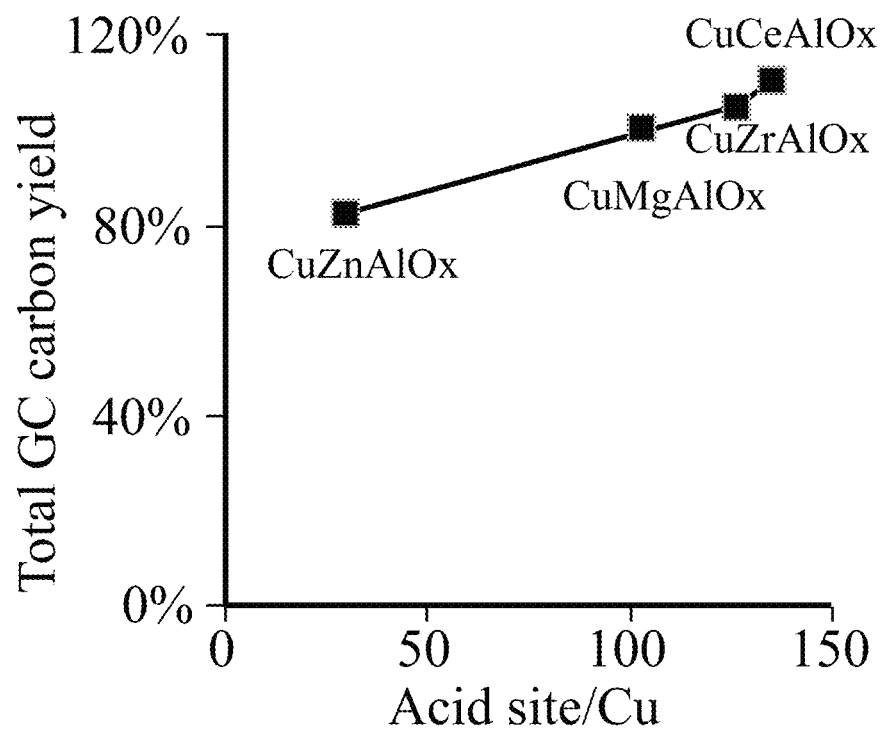
FIG. 10 illustrates the correlation between acid site density with total GC carbon yield, according to some embodiments of the present disclosure. Reaction condition: Reaction condition: batch, 1.2 g sorbitol, reduced mixed oxide catalyst, 30 mL methanol, 300° C., 2 h, sorbitol carbon:Cu=63:1 (mol basis).

The effect of catalyst porosity was evaluated by comparing the total light oxygenate product yield with various Cu-based mixed oxides when using biomass and sorbitol monomer (i.e., sugar alcohol produced by the reaction of glucose) as the feedstock (see FIG. 7). For all catalysts tested, the total light oxygenate carbon yield increased when sorbitol was the reactant, likely due to the absence of the solvolysis step. Carbon yield from biomass appears to correlate with catalyst porosity with the optimal at an average pore size of about 5 nm for CuCeAlO$_x$ (see FIG. 8). Smaller pores (<4 nm, e.g., CuZrAlO$_x$) may cause diffusion limitations of sugar oligomers and larger pores (>12 nm e.g., CuMgAlO$_x$ and CuZnAlO$_x$) may facilitate coke formation. On the other hand, the conversion of sorbitol was comparable among the catalyst supports (100-110%), except for CuZnAlO$_x$ (83%). Due to the small kinetic diameter of sorbitol (~8 Å), diffusion is likely not a determining factor and the carbon yield seems to be more dependent on catalyst acidity. NH$_3$ TPR measurements show that the acid density is comparable among CuMgAlO$_x$, CuZrAlO$_x$ and CuCeAlO$_x$ (103, 127, 135 mol acid site/mol Cu respectively) and is the lowest for CuZnAlO$_x$ (30 mol acid site/mol Cu), which may explain the catalyst's low carbon yield (see FIGS. 9 and 10). By unveiling the role of catalyst porosity and acidity on the total light product yield, a material design strategy emerges that can increase activity and lower energy demand in a cellulosics conversion process, as is also the case, as shown above, for oxide support reducibility. In a scaled-up process, where solvolysis and catalysis steps are decoupled, and feedstock variation may occur, depolymerization of cellulosics may change at a fixed reaction condition. In that context, understanding the optimal catalyst pore size for a certain dp of the sugar oligomers may be important to alleviate variation in catalyst performances. In addition, minimizing coke formation may help prolong catalyst lifetime and reduce process downtime.

Figure 11A:
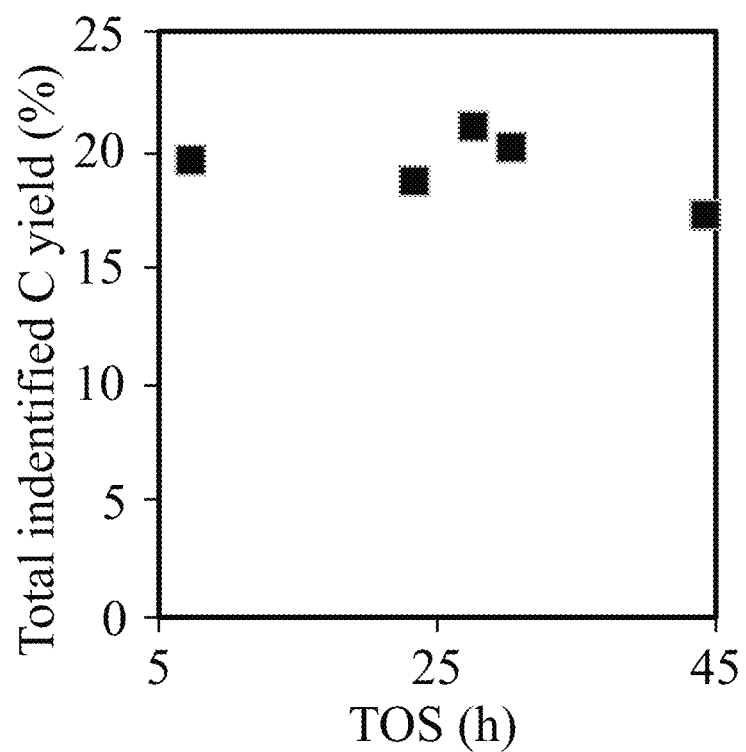
FIG. 11A illustrates the time on stream profile of total identified carbon yield, according to some embodiments of the present disclosure. Reaction condition: 3 wt % solvolyzed delignified hybrid poplar in methanol feed, 0.12 mL/min, 300° C., 3000 psi, 0.2 g reduced $CuZnAlO_x$.
Figure 11B:
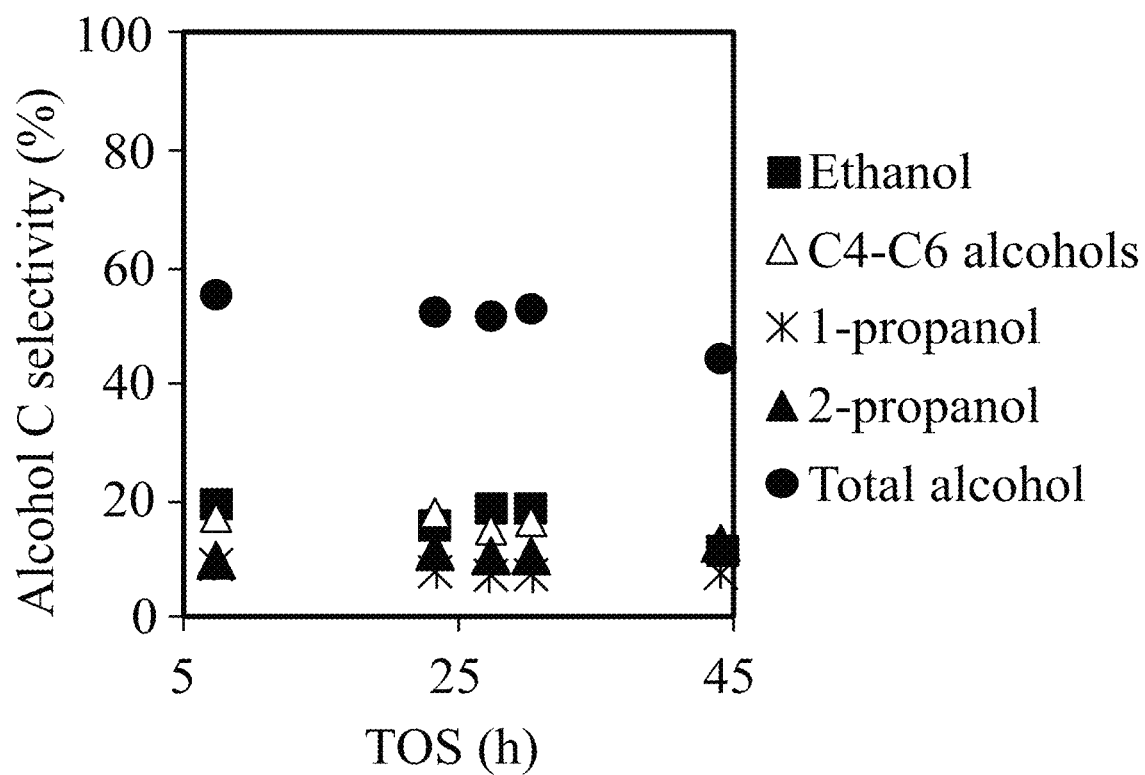
FIG. 11B illustrates the time on stream profile of C2-C6 alcohol selectivity, according to some embodiments of the present disclosure. Reaction condition: 3 wt % solvolyzed delignified hybrid poplar in methanol feed, 0.12 mL/min, 300° C., 3000 psi, 0.2 g reduced $CuZnAlO_x$.
Figure 12:
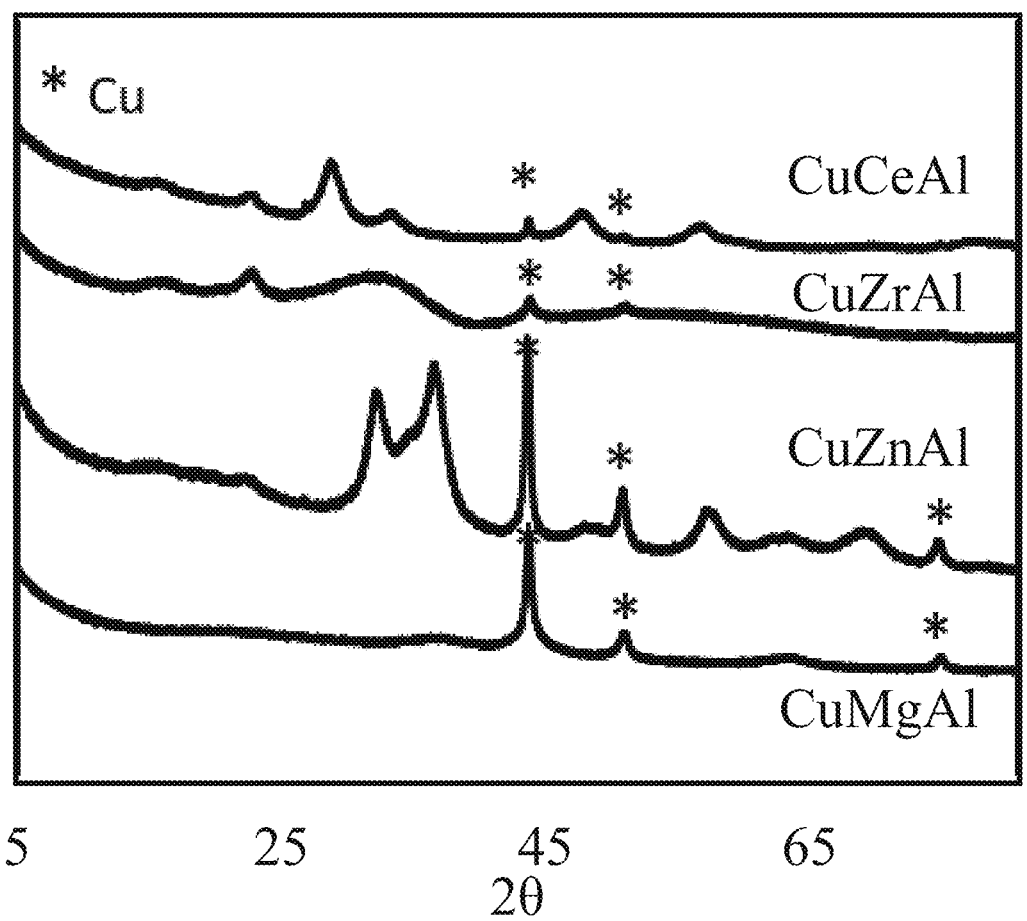
FIG. 12 illustrates XRD spectra of copper-based oxide catalysts, according to some embodiments of the present disclosure.
Figure 13:
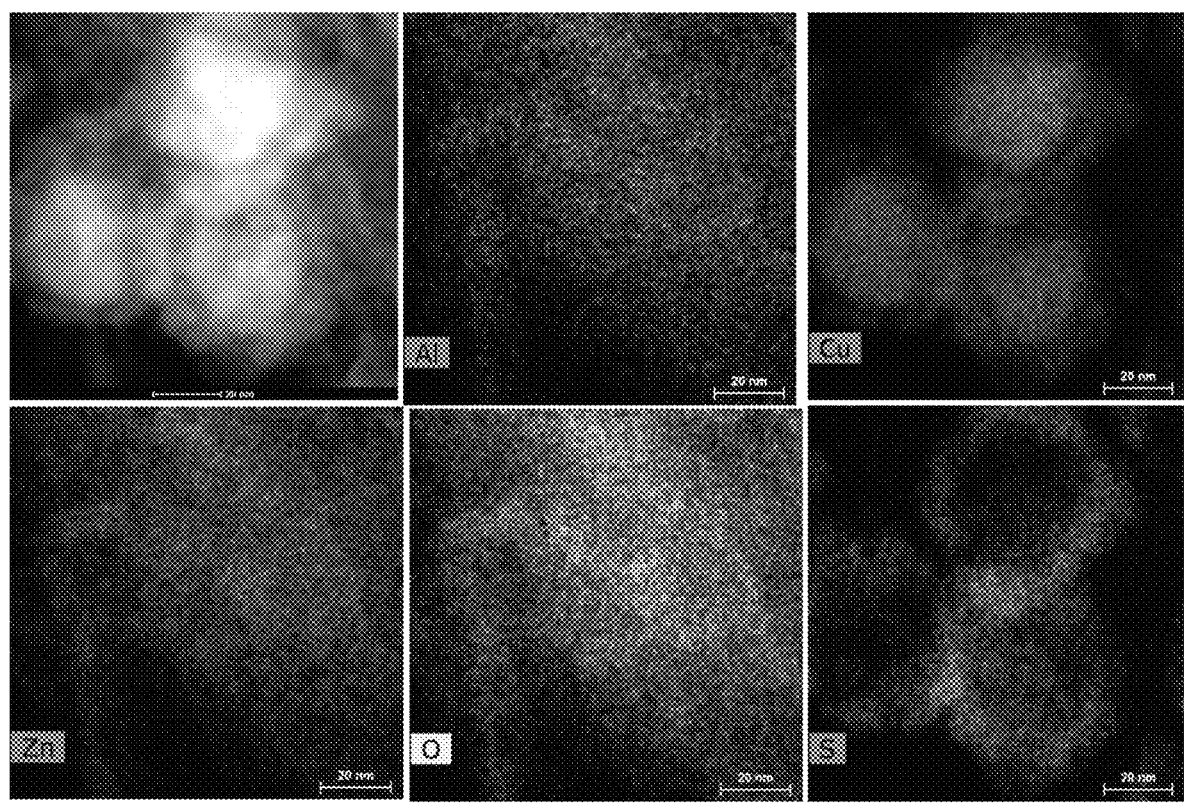
FIG. 13 illustrates scanning transmission electron microscopy with high angle annular dark field (STEM-HAADF) detector images of spent $CuZnAlO_x$ catalyst, according to some embodiments of the present disclosure.

Catalyst stability: The stability of copper-based oxide catalysts was evaluated in a continuous flow reactor with 3 wt % solvolyzed delignified hybrid poplar in methanol as the feedstock. Results for CuZnAlO$_x$ for 45 hours on stream (TOS) shows that the catalyst was stable at the testing conditions at low carbon yield of 20% (see FIGS. 11A and 11B). However, XRD spectra of the spent catalyst showed presence of ~100 nm Cu particles, indicative of Cu thermal sintering (see FIG. 12) that were initially <5 nm in diameter, as indicated by XRD. The growth of Cu nanoparticle after reactions were also captured in SEM-EDS images (see FIG. 13; scale bar=20 nm).

Figure 14:
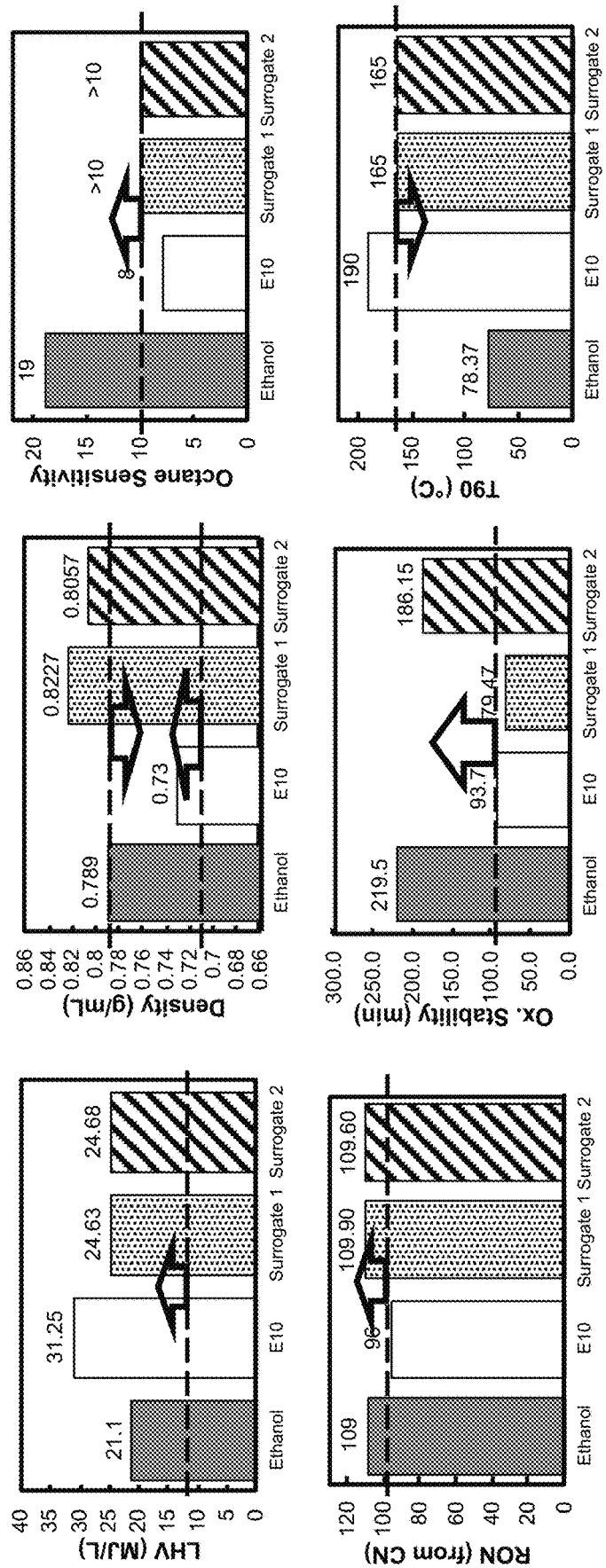
FIG. 14 illustrates experimentally measured fuel properties of surrogate mixtures for products produced in Step 2 of FIG. 1 using $CuZnAlO_x$, according to some embodiments of the present disclosure. Surrogate 1: top 20 products listed in Table 2. Surrogate 2: top 12 alcohol products listed in Table 2.

Fuel properties: The C2-C6 aliphatic alcohols product of direct catalytic conversion of cellulose have high grade fuel properties. However, the fuel values of the product mixtures, which contain other oxygenate functionalities, such as ketones, esters, furanics and hydrocarbons, have not been evaluated. As described herein, the fuel properties of surrogate fuels were measured under a range of blend levels into reformulated blendstocks for oxygenate blending (RBOB) base fuels (up to 30% and pure). The fuel properties of interest include research octane number (RON), octane sensitivity, density, cloud/freeze point, 90% distillation temperature (T90), oxidative stability, lower heating value (LHV), and Reid vapor pressure (RVP), and are compared against E10 fuel as a baseline. The current available data for two surrogate fuel mixtures with similar composition to the light oxygenate product mixture of the DC3 reactions catalyzed by CuZnAl are shown in FIG. 14. Surrogate 1 included the top 20 products of the product mixture and Surrogate 2 contained only the 12 alcohol components of the top 20, with the exception of 1,2-butanediol (see Table 2). Both surrogates met the criteria (shown in arrows) for boosted SI and out-perform E10 in term of RON, octane sensitivity and T90. However, oxidative stability of Surrogate 1 (9.47 mins) was slightly lower than E10 (93.7 mins) and much lower than Surrogate 2 (186.15 mins). This finding indicates the negative impact of functionalities other than alcohol in fuel values of the liquid product mixtures produced in Step 2 of FIG. 1. Therefore, higher alcohol selectivity is desirable and can be realized with some embodiments of catalysts described herein to provide additional benefit of boosting energy density (LHV).

TABLE 2

Figure 2:
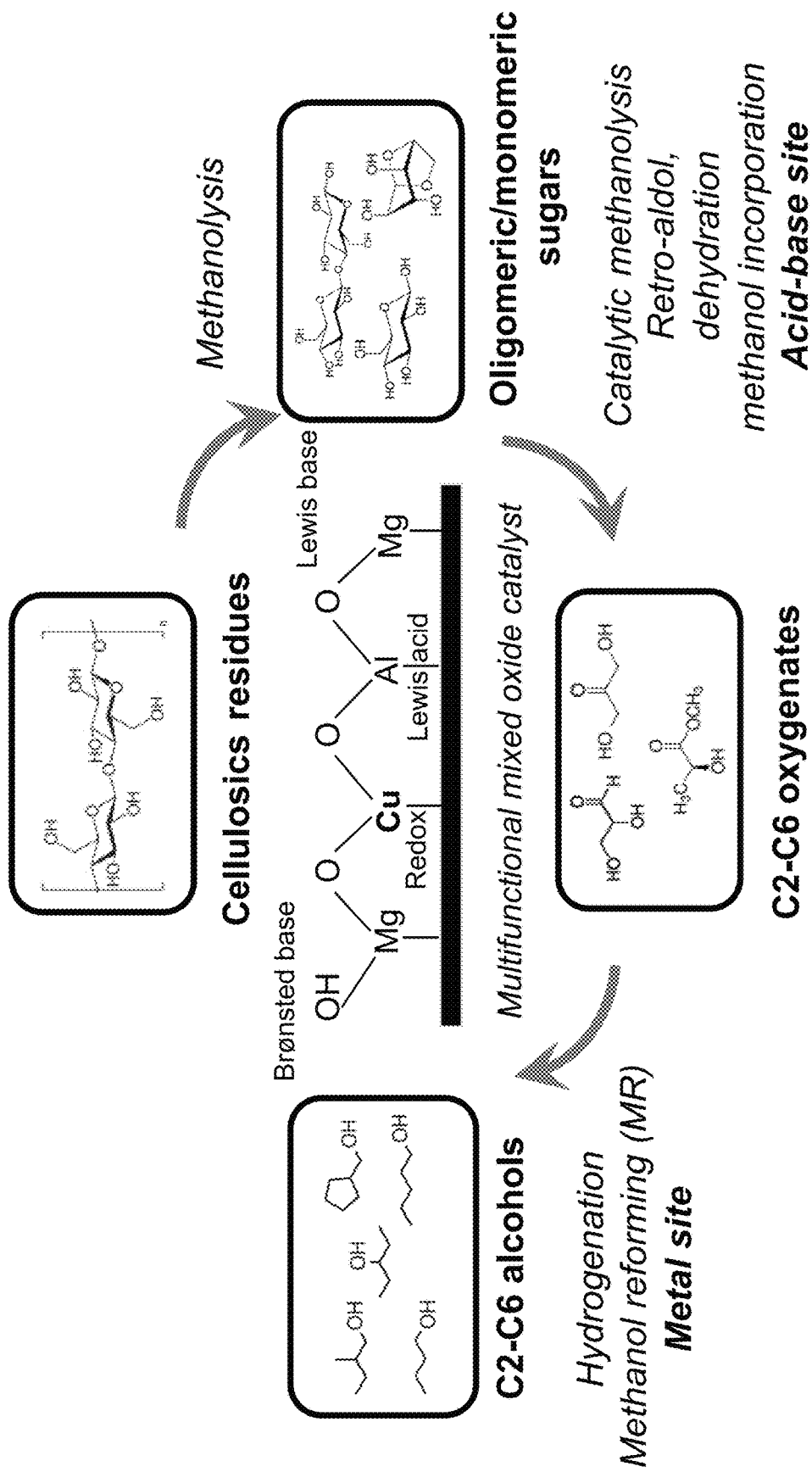
FIG. 2 illustrates a reaction network for Step 2 of FIG. 1, according to some embodiments of the present disclosure.

List of components in Surrogate 1 and Surrogate 2 (italicized) for products from Step 2 of Figure 1

| # | Name | Structure | Concentration (mol/L) |
|---|---|---|---|
| 1 | *ethanol* | 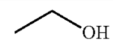 | 0.0941 |
| 2 | methyl acetate | 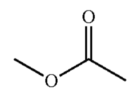 | 0.0094 |
| 3 | *2-propanol (i.e. isopropanol)* | 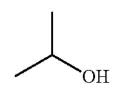 | 0.0096 |
| 4 | *1-propanol* | 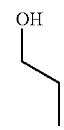 | 0.0264 |
| 5 | 2-methyl furan | 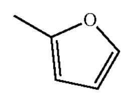 | 0.0049 |
| 6 | *2-Butanol* | 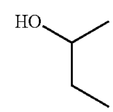 | 0.0082 |
| 7 | methyl propionate | 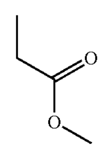 | 0.0049 |
| 8 | *isobutanol* | 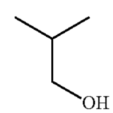 | 0.0206 |
| 9 | *1-butanol* | 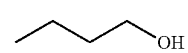 | 0.0076 |
| 10 | *3-methyl-2-butanol* | 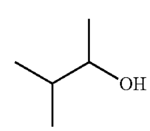 | 0.0035 |
| 11 | methyl butyrate | 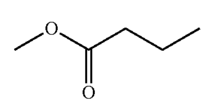 | 0.0019 |
| 12 | *2-methyl-1-butanol* | 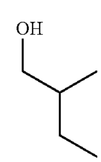 | 0.0162 |

TABLE 2-continued

List of components in Surrogate 1 and Surrogate 2 (italicized) for products from Step 2 of Figure 1

| # | Name | Structure | Concentration (mol/L) |
|---|---|---|---|
| 13 | 3-hexanone | 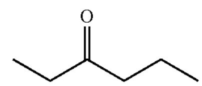 | 0.0023 |
| 14 | *2-methyl-2-pentanol* | 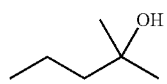 | 0.0015 |
| 15 | *1-pentanol* | 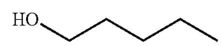 | 0.0038 |
| 16 | 2-methyl(methyl butanoate) | 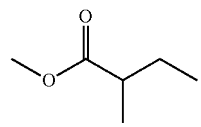 | 0.0015 |
| 17 | *1,2-butanediol* | 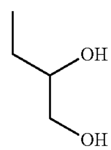 | 0.0012 |
| 18 | *3-hexanol* | 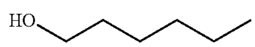 | 0.0019 |
| 19 | Methyl Valerate (i.e. methyl pentanoate) | 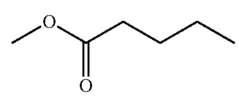 | 0.0019 |
| 20 | 2-Methylcyclopentanone | 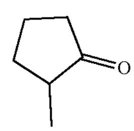 | 0.0050 |

Surrogate 1: #1-20
Surrogate 2: *Italicized*

Advantages of some embodiments of the present disclosure include a $CuCeAlO_x$ catalyst that enables a higher alcohol yield compared to other catalysts for the same contact time, during reactions like Step in FIG. 1. This is true regardless of biomass type due to how the catalyst interacts with methanol and the solvolyzed intermediates. Catalysts as described herein function when contacting biomass and supercritical methanol, as well as when first solvolyzing the biomass in methanol at subcritical conditions and then running the liquid slurry over the catalyst. Further, the catalysts described herein are not limited to biomass and the catalyst will work with other carbon feedstocks (e.g., plastics). In addition, the catalysts described herein will work with methanol and methanol including other solvents mixed with methanol (ethanol, propanol, water, etc.).

Initially, three $CuMAlO_x$ mixed oxide (M=Mg, Zr, Ce) catalysts were synthesized with varying reducibility. Mg, Zr, and Ce (incorporated into the catalyst as MgO, $ZrO_2$, and $CeO_2$). $Al_2O_3$ was kept as the common metal oxide to all catalysts since, among other things, it is irreducible. The molar metal content was kept constant at Cu:M:Al equal to about 1:4:1.67 so changes in catalyst properties could be evaluated as a function of varying M. Correspondingly, catalyst properties and activity were normalized by the bulk Cu metal molar content. In addition, three $MAlO_x$ mixed oxides without Cu were synthesized and evaluated as controls.

Figure 15A:
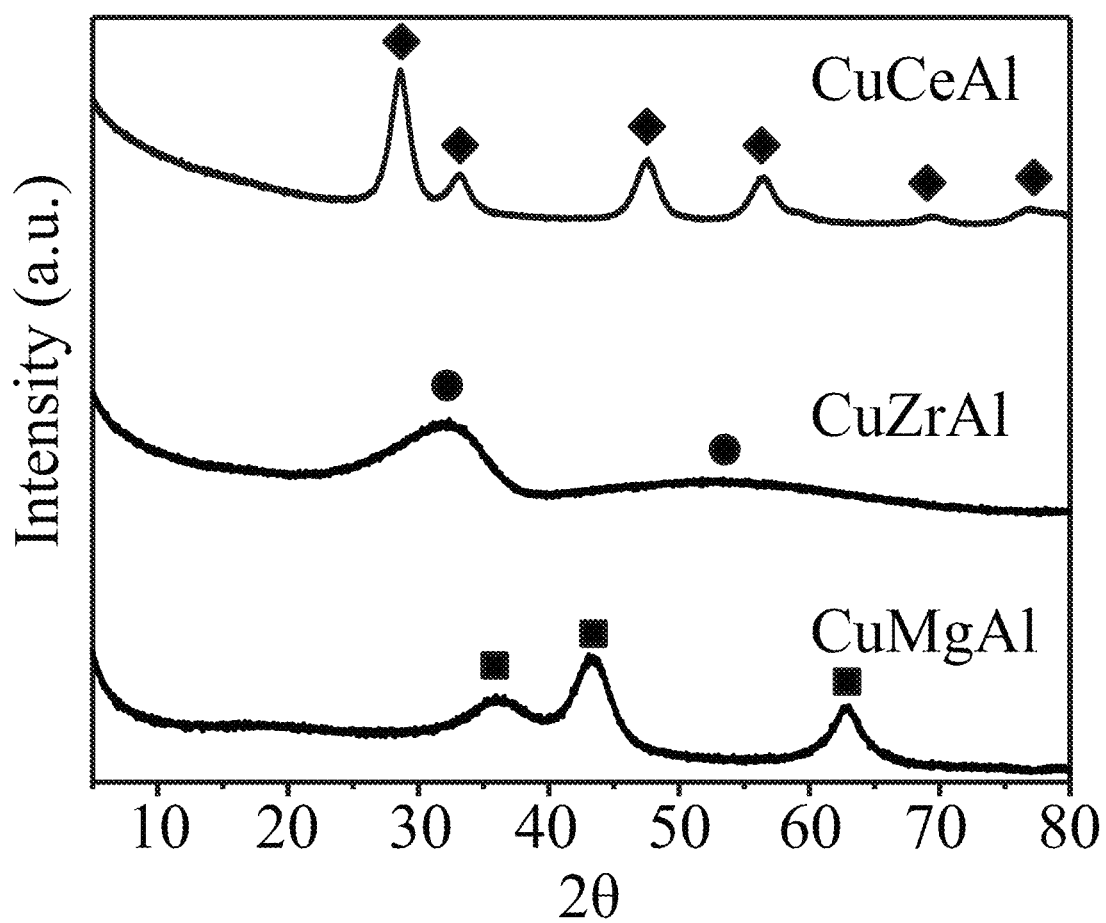
FIG. 15A illustrates crystallinity data as measured by XRD of $CuMAlO_x$ of, ■: MgO, ●: $ZrO_2$, ◆: $CeO_2$, according to some embodiments of the present disclosure.

Elemental analysis confirmed the experimental metal content reasonably agreed with the target metal composition (Table 3). The catalysts exhibited comparable BET surface area (between about 180 $m^2/g$ and about 222 $m^2/g$), and meso-porosity to provide small sugar oligomers and other intermediates accessibility to the catalyst active sties. Crystallinity patterns by XRD suggest that metallic Copper nanoparticles were well dispersed and below the detection limit of XRD 5 nm) (see FIG. 15A). Thus, in some embodiments of the present disclosure, copper nanoparticles are dispersed on the surface of the copper-based mixed metal oxide catalysts.

TABLE 3

Elemental content, BET surface area, BJH pore volume and pore size, acid density and basic density of $CuMAlO_x$

|  | $CuMgAlO_x$ | $CuZrAlO_x$ | $CuCeAlO_x$ | $MgAlO_x$ | $ZrAlO_x$ | $CeAlO_x$ |
|---|---|---|---|---|---|---|
| BET surface area ($m^2/g$) | 222.3 | 179.2 | 188.7 | 264.6 | 140.3 | 146.7 |
| BJH pore volume ($cm^3/g$) | 1.20 | 0.11 | 0.46 | 1.55 | 0.09 | 0.47 |
| Average pore size (nm) | 18.3 | 3.4 | 5.7 | 13.0 | 3.3 | 3.9 |
| (Cu:M:Al) molar ratio | 1:3.5:16 | 1:3.9:16 | 1:4.5:1.7 | 0:3.0:1 | 0:2.9:1 | 0:2.9:1 |
| Cu (wt %) | 18 | 10 | 6 | 0 | 0 | 0 |
| Acid site ratio (mol/mol Cu) | 0.1028 | 0.1268 | 0.1350 | N/A | N/A | N/A |
| Acid site density ($\mu mol/g$) | 291.3 | 206.1 | 126.7 | 146.3 | 162.5 | 113.8 |
| Basic site ratio (mol/mol Cu) | 0.022 | 0.015 | 0.025 | N/A | N/A | N/A |
| Basic site density ($\mu mol/g$) | 61.11 | 28.9 | 40.1 | 146.7 | 78.8 | 136.6 |

Figure 15B:
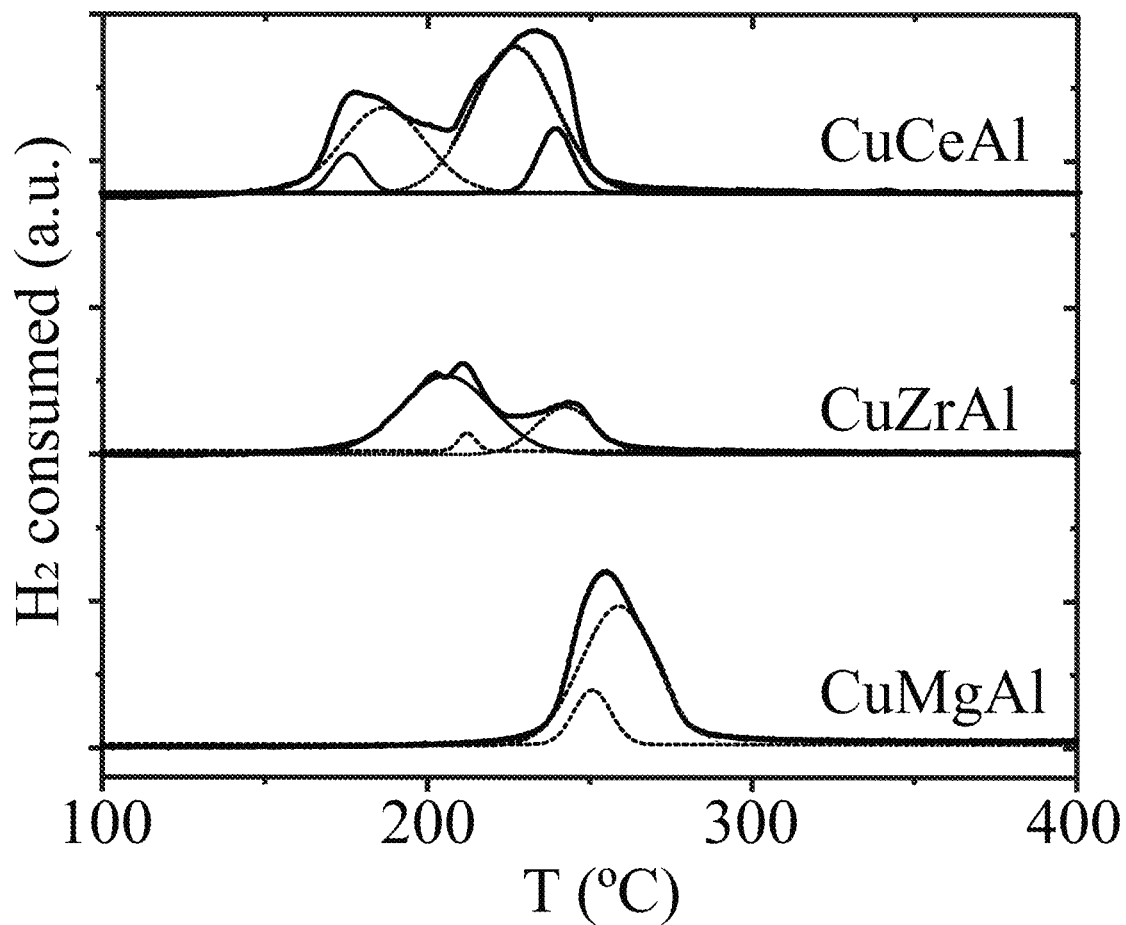
FIG. 15B illustrates a reducibility profile as measured by $H_2$ TPR of $CuMAlO_x$, according to some embodiments of the present disclosure.
Figure 16A:
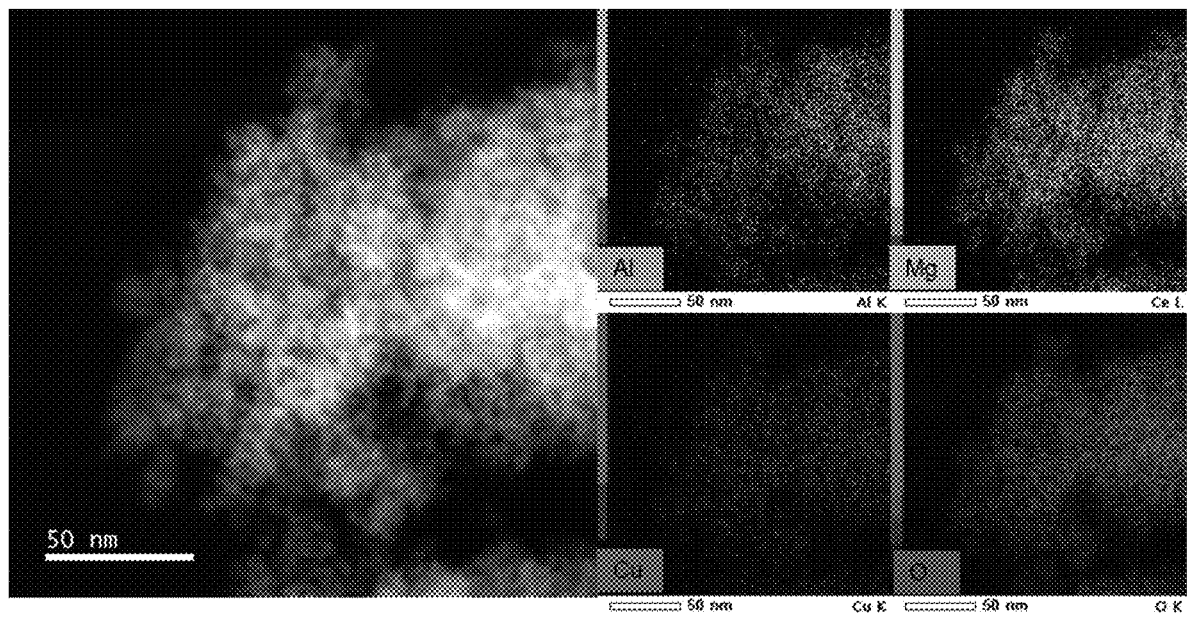
FIG. 16A illustrates STEM-EDS images of reduced $CuMgAlO_x$, according to some embodiments of the present disclosure.
Figure 16B:
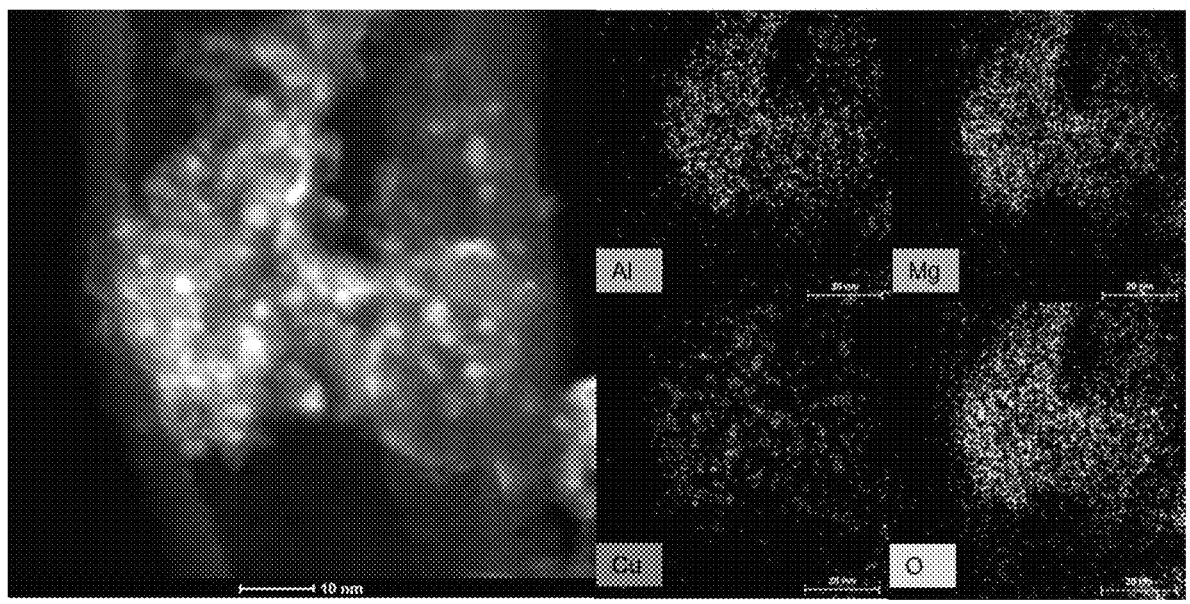
FIG. 16B illustrates STEM-EDS images of reduced $CuCeAlO_x$, according to some embodiments of the present disclosure.

Changing the metal "M" significantly increased the reducibility of the $CuMAlO_x$ catalysts, as confirmed by oxygen vacancy capacity and reduction temperatures during $H_2$ TPR experiments (see FIG. 15B). The extent of oxygen vacancy formation via $H_2$ spillover was indicated by the measured $H_2$ consumption ($H_{2-exp}$) that surpassed the theoretical $H_2$ amount required for complete CuO reduction to $Cu^0$ ($H_{2-theo}$, equivalent to bulk Cu content). The $H_{2-exp}/H_{2-theo}$ ratio increased in the order of 1~Mg<Zr~1.5<Ce~3.4. This is consistent with the uniform distribution of metal elements observed in the associated STEM images (see FIGS. 16A and 16B). The trend in reducibility of the $CuMAlO_x$ coincides with the reducible properties of the support oxide "M", which can potentially serve as a design parameter.

Figure 15C:
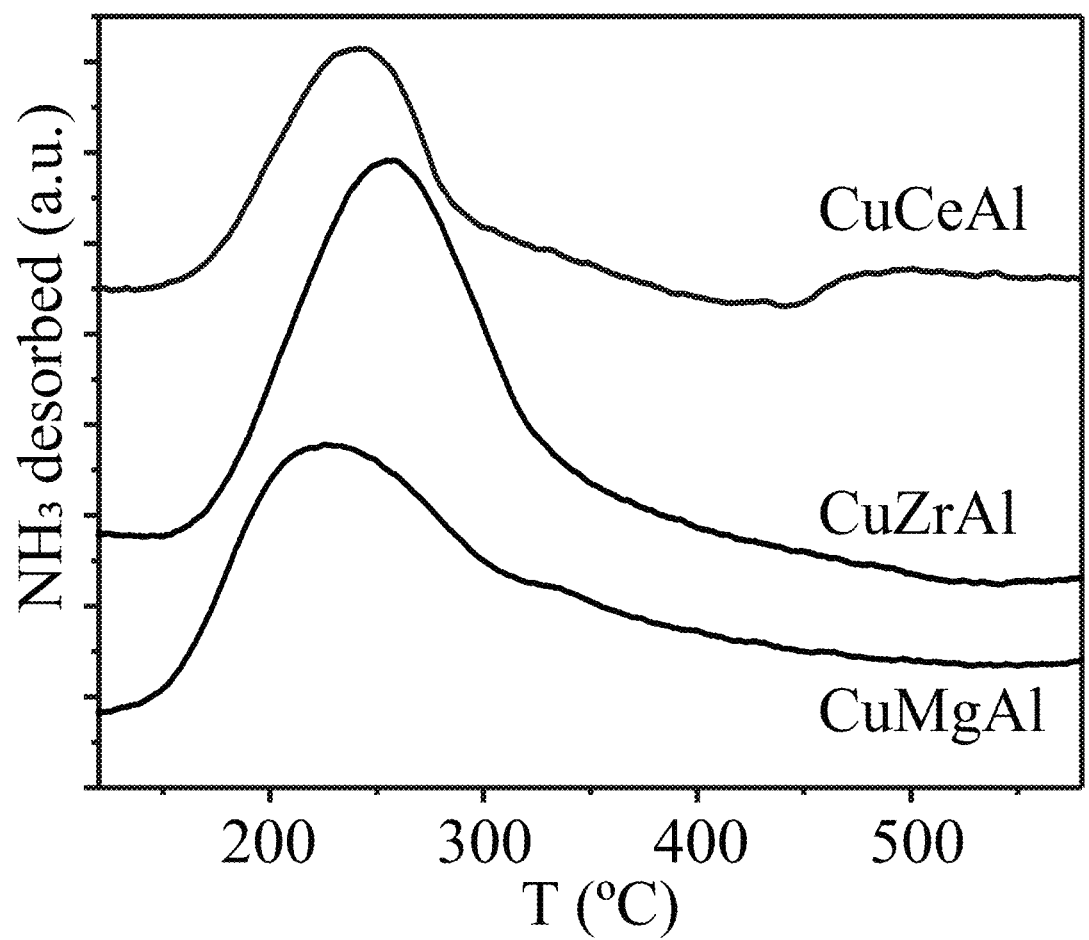
FIG. 15C illustrates acidity data as measured by $NH_3$ TPR data of $CuMAlO_x$, according to some embodiments of the present disclosure.
Figure 15D:
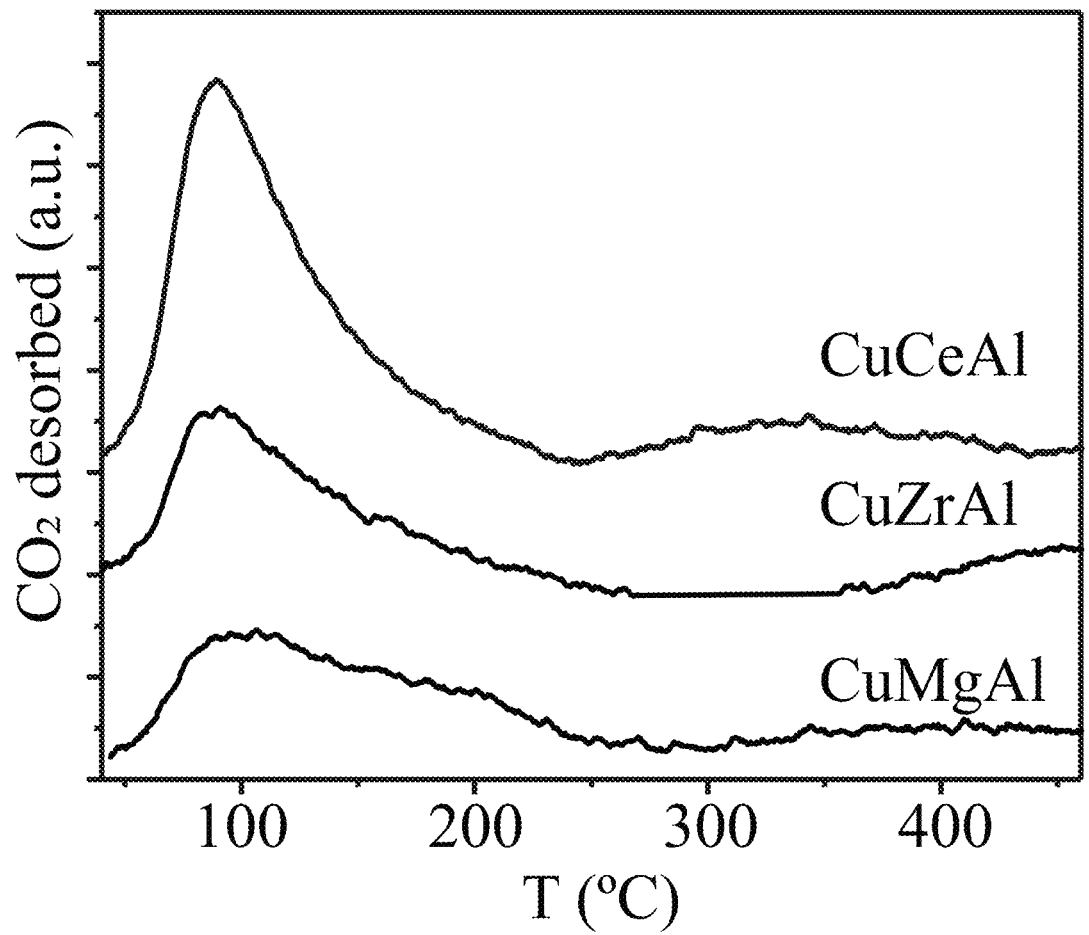
FIG. 15D illustrates basicity data as measured by $CO_2$ TPD data of $CuMAlO_x$, according to some embodiments of the present disclosure.
Figure 17A:
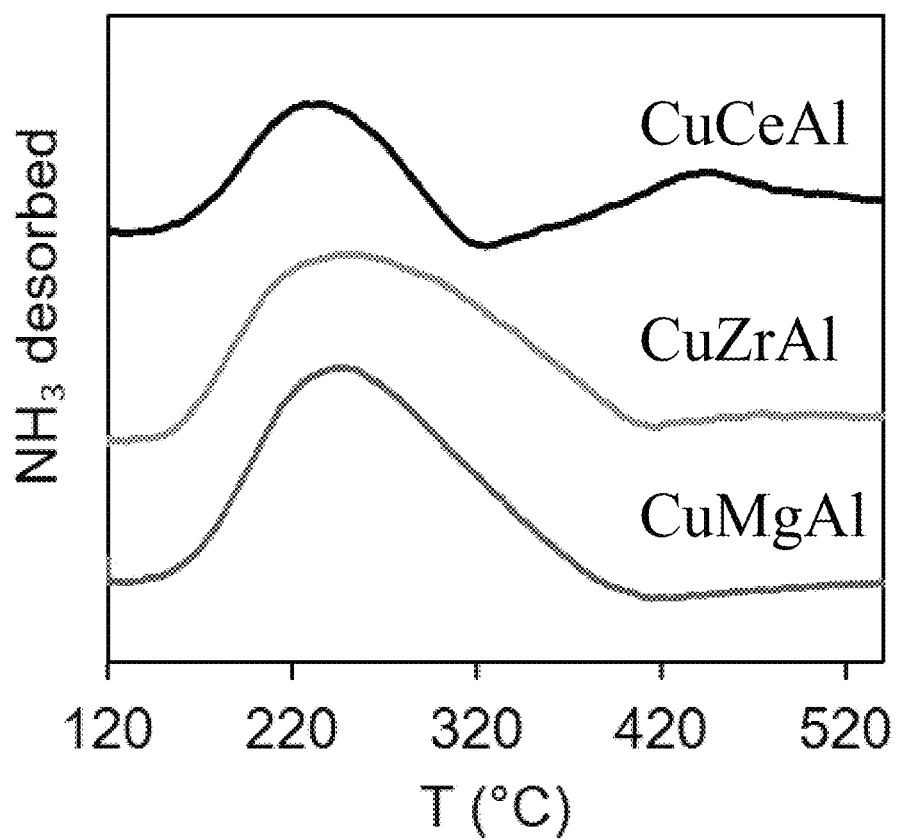
FIG. 17A illustrates chemisorption acidity data of $MAlO_x$ catalyst as measured by measured by $NH_3$ TPD, according to some embodiments of the present disclosure.
Figure 17B:
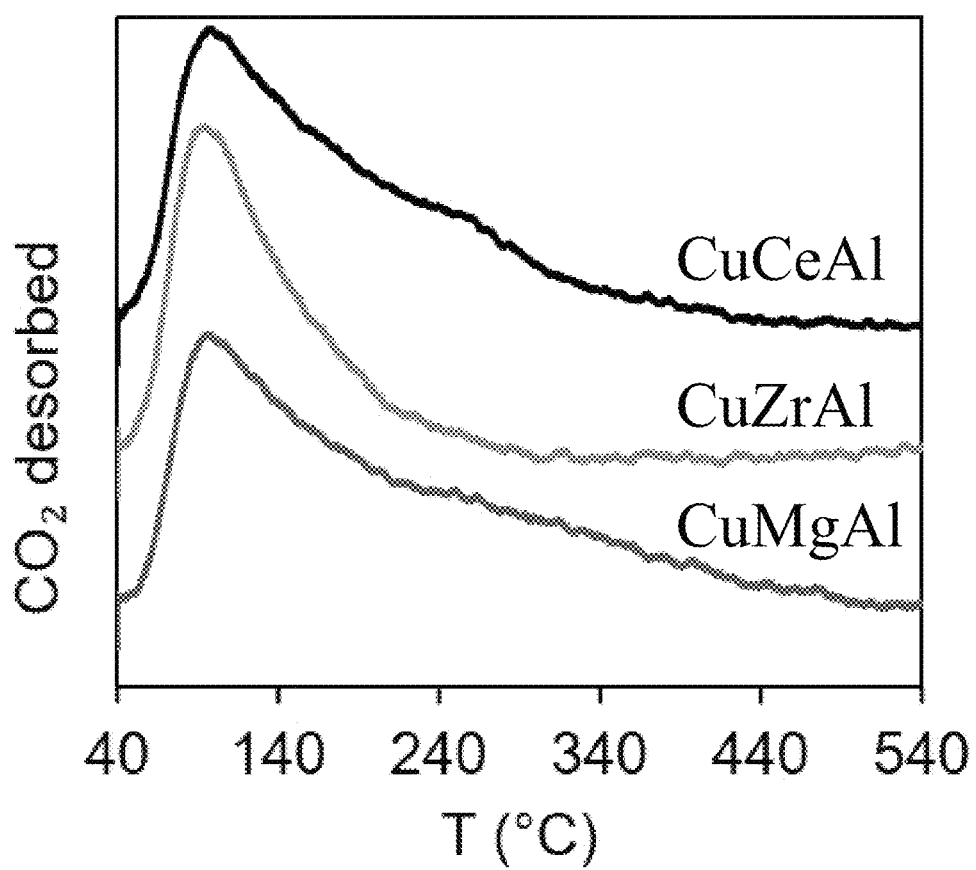
FIG. 17B illustrates chemisorption basicity data of $MAlO_x$ catalyst as measured by $CO_2$ TPD, according to some embodiments of the present disclosure.

In contrast, the measured acidity and basicity of the catalysts showed a weak dependence on "M", with Cu (see FIGS. 15C and 15D) or without Cu (see FIGS. 17A and 17B). The very low concentration of weakly adsorbed $CO_2$ suggests basic sites may play a negligible role for influencing trends in catalyst performance. Broad $NH_3$ desorption peaks in the temperature range between about 200° C. and about 250° C. suggest weak Lewis acidity for all catalysts. The presence of Cu marginally enhanced the strength of the Lewis acid sites, indicated by slight shifts to higher desorption temperatures of $CuMAlO_x$ compared to $MAlO_x$. Ce-containing catalysts displayed additional $NH_3$ TPD peaks in the range between about 443° C. and about 480° C., which may be attributed to stronger acid sites.

Synthesized catalysts were tested in batch reactors for SCM-DHDO of cellulosic residues produced from the delignification of hybrid poplar. The delignified biomass contains the intact (hemi)cellulose portion and 19% of lignin residues, as determined by. SCM-DHDO catalyst activity was evaluated based on the $C_2$-$C_7$ light alcohol carbon yield. To normalize the observed activity of $CuMAlO_x$ with experimental bulk Cu content, the Cu-to-biomass loading was fixed at about 3.8 wt %. As noted above, the Cu to "M" molar ratio was fixed at about 1:4, which corresponded to a catalyst loading of about 20, 36 and 63 wt % for $CuMgAlO_x$, $CuZrAlO_x$, $CuCeAlO_x$ respectively, since the atomic mass of Mg<Zr<Ce. Similarly, for $MAlO_x$, the Al-to-biomass loading was fixed at about 2.6 wt %, similar to the aluminum loading of $CuMAlO_x$.

Figure 18A:
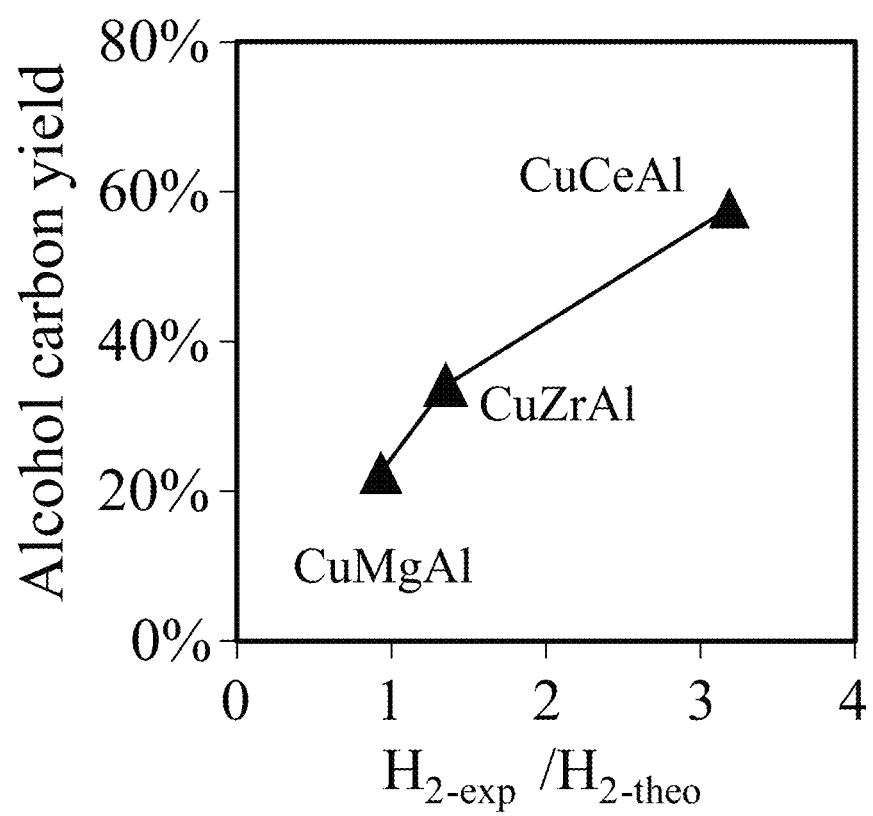
FIG. 18A illustrates a correlation between alcohol yield and the reducibility of $CuMAlO_x$, according to some embodiments of the present disclosure. Reaction conditions: 1 g delignified hybrid poplar, reduced $CuMAlO_x$, 3.8 wt % Cu loading, 30 mL methanol, 300° C., 250 psi $N_2$ loaded at room temperature, 2 h duration (not including 70 min of heat-up time).
Figure 18B:
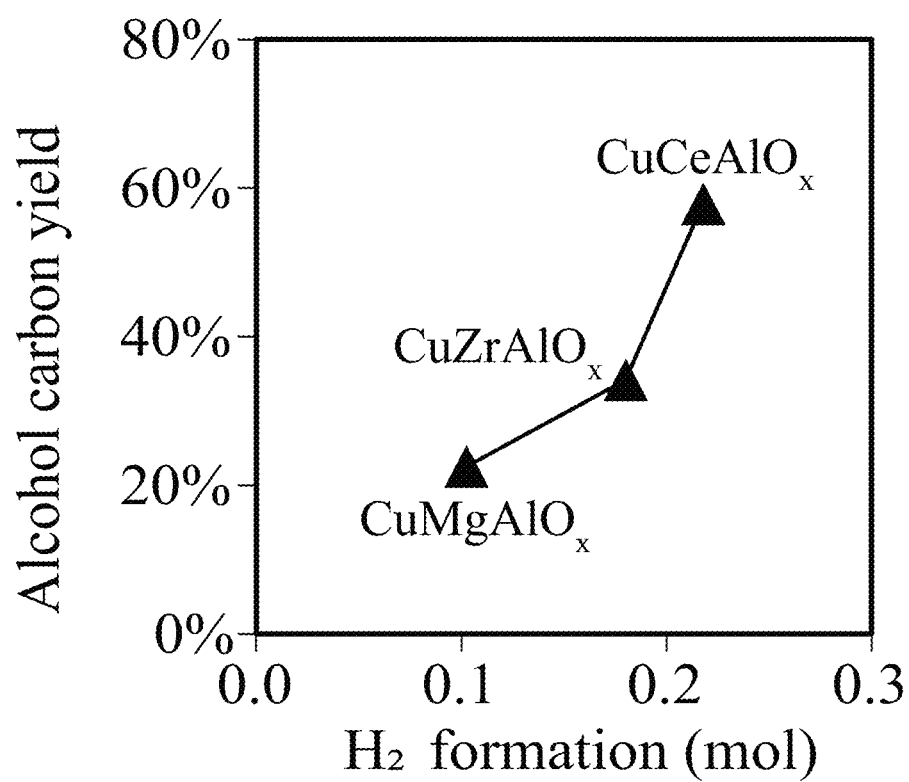
FIG. 18B a correlation between alcohol carbon yield and $H_2$ formation by methanol reforming of $CuMAlO_x$, according to some embodiments of the present disclosure. Reaction conditions the same as listed for FIG. 18A.
Figure 19A:
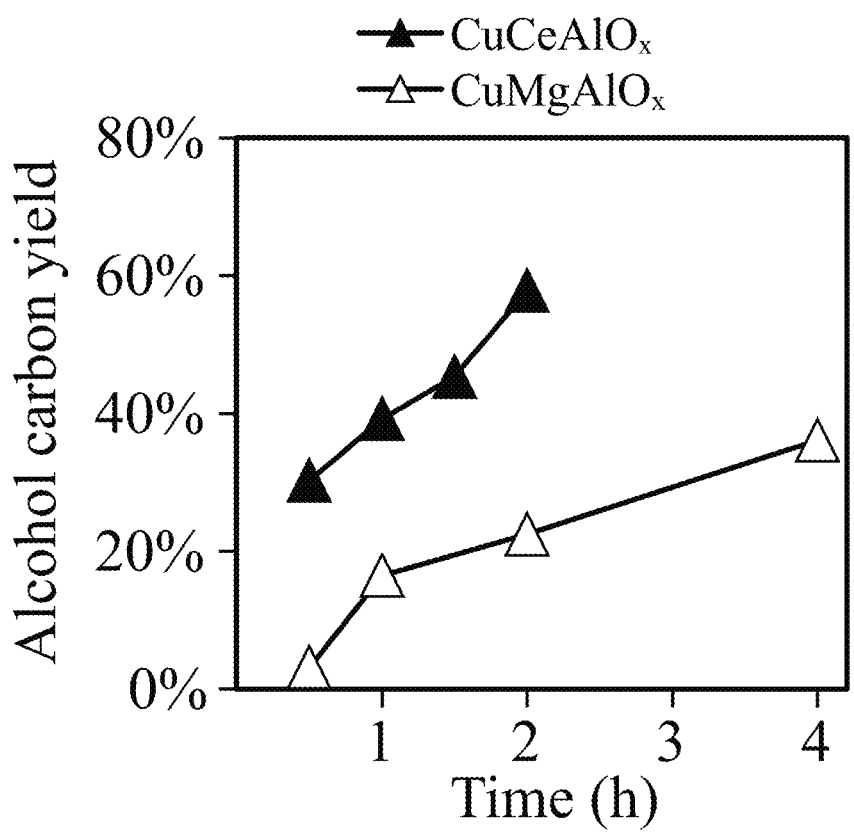
FIG. 19A illustrates a temporal profile of SCM-DHDO batch reactions of delignified hybrid poplar by reduced $CuCeAlO_x$ and $CuMgAlO_x$, according to some embodiments of the present disclosure. Reaction conditions: 1 g delignified hybrid poplar, reduced $CuMAlO_x$, 3.8 wt % Cu loading, 30 mL methanol, 300° C., 250 psi $N_2$, t=[0.5-4 h] (not including 70 mins of heat-up time).

Among the $CuMAlO_x$ catalysts, the $C_2$-$C_7$ alcohol yield increased with the reducibility ($H_{2-exp}/H_{2-theo}$ ratio), in the order of $CuMgAlO_x$ (22%)<$CuZrAlO_x$ (34%)<$CuCeAlO_x$ (58%) (see FIG. 18A). The greater than two-fold enhancement in alcohol yield observed when replacing Mg with Ce was further confirmed by measuring the alcohol formation rate from their temporal profiles (see FIG. 19A). The trend in $H_2$ formation from methanol reforming followed the same fashion (see FIG. 18B). This correlation suggests that hydrogenation of unsaturated oxygenates and methanol reforming were accelerated by surface oxygen vacancies on the support "M" oxide. Therefore, a potential design criterion for SCM-DHDO Cu-based catalyst may be reducibility, which coincided with reducible property of the stand-alone "M" oxide.

Figure 18C:
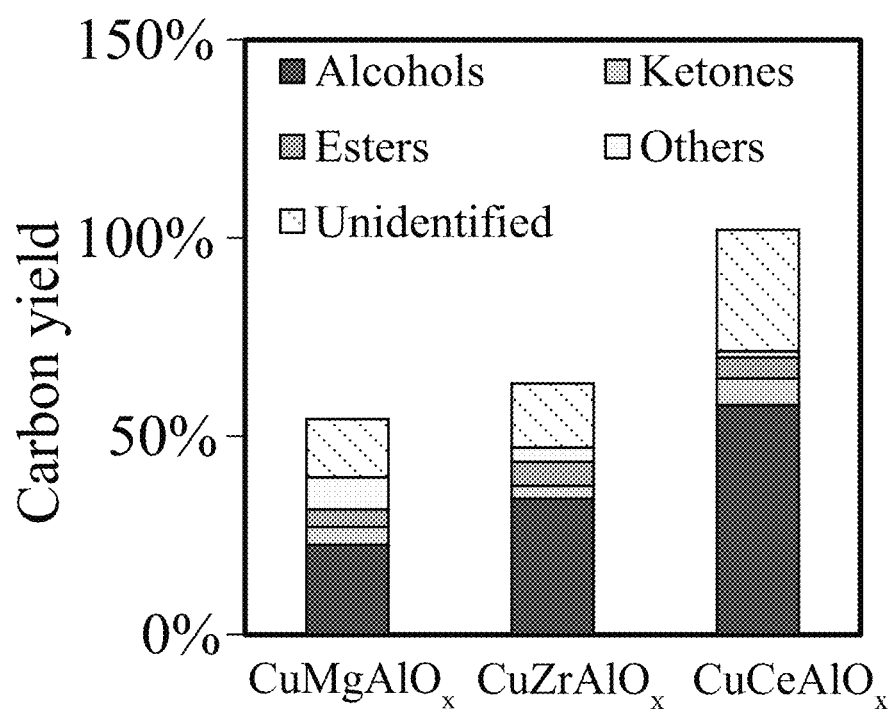
FIG. 18C illustrates carbon yield of light oxygenate products in a batch reaction by $CuMAlO_x$, according to some embodiments of the present disclosure. Reaction conditions the same as listed for FIG. 18A.
Figure 19B:
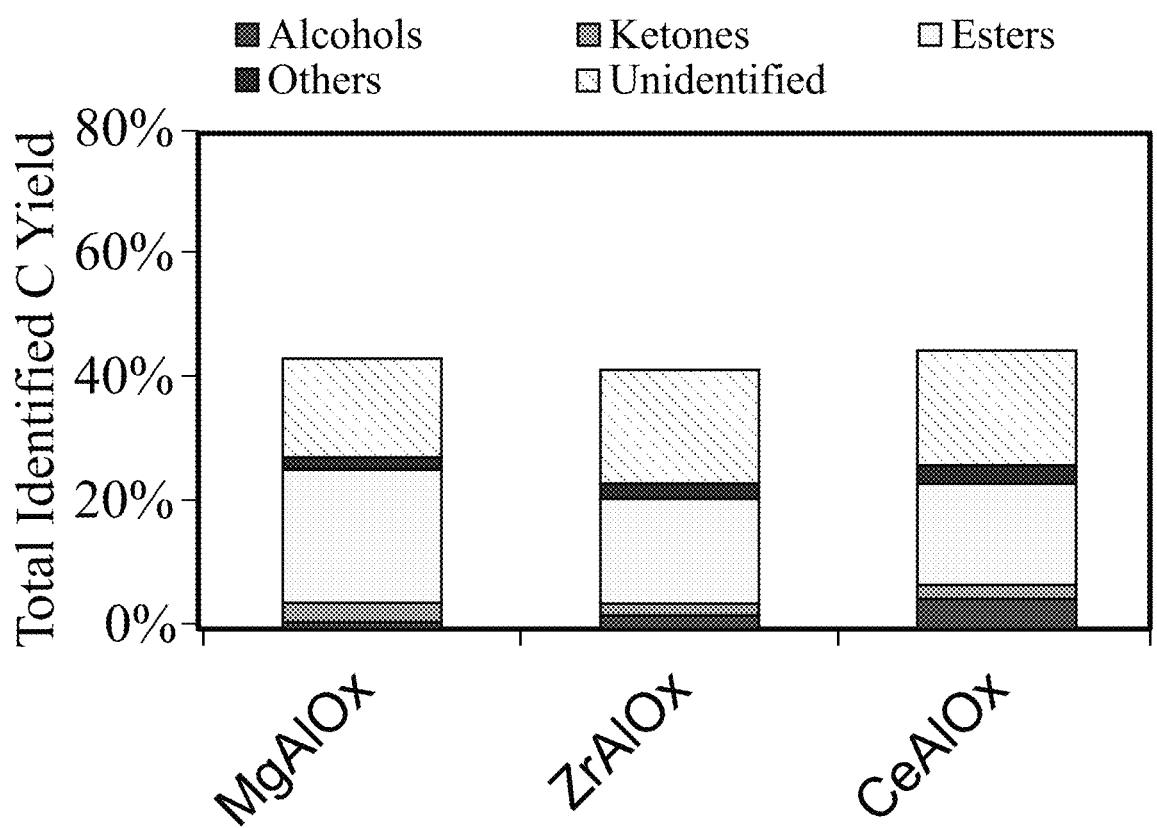
FIG. 19B illustrates carbon yield of light oxygenate products of SCM-DHDO batch reactions of delignified hybrid poplar by $MAlO_x$, according to some embodiments of the present disclosure. Reaction conditions: 1 g delignified hybrid poplar, $MAlO_x$, 2.6 wt % Al loading, 30 mL methanol, 300° C., 250 psi $N_2$, t=2 h (not including 70 mins of heat-up time).

The synergistic effect of Cu site with reducibility was indicated by the very low alcohol yield (up to 5%) by the $MAlO_x$ (see FIG. 19B). Additionally, while the total light oxygenate yields were comparable among the $MAlO_x$ (42-46%), it was enhanced with the presence of Cu (see FIG. 18C). This indicates that hydrogenation likely shifted equilibrium of C—C bond cleavage of sugar oligomers, while the chemistries were insensitive to changing "M", due to the relatively similar acidity and basicity between the catalysts.

Figure 18D:
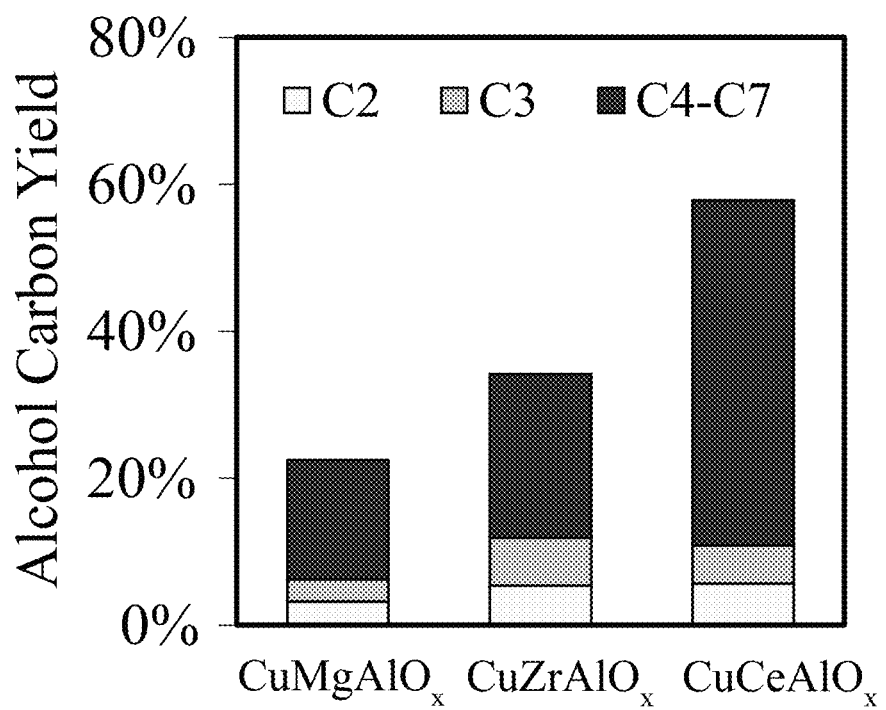
FIG. 18D illustrates alcohol carbon yield by carbon number of batch reaction by $CuMAlO_x$, according to some embodiments of the present disclosure. Reaction conditions the same as listed for FIG. 18A.

Light liquid oxygenate compositions varied with M in $CuMAlO_x$, demonstrating the potential for catalyst design to tune the product slate (see FIG. 18C). Besides $C_2$-$C_7$ alcohols, the $C_2$-$C_{10}$ light (GC-detectable) liquid products also consisted of $C_2$-$C_7$ ketones, esters, and others, including ethers, diols, furanics, and heavier ($\geq C_8$) aromatics. The unidentified carbon yield ranged from 15-35%, depending on the catalyst (detailed product compositions listed in Table 4). $CuCeAlO_x$ exhibited noticeably higher alcohol selectivity (79%) and higher content of $C_4$-$C_7$ alcohols (81%) (see FIG. 18D). The predominance of these energy dense alcohols and trace amounts of unsaturated oxygenates can significantly impact fuel properties, as discussed below.

TABLE 4

SCM-DHDO liquid product composition by CuMAlO$_x$ in batch.

| CuMgAlO$_x$ | | CuZrAlO$_x$ | | CuCeAlO$_x$ | |
|---|---|---|---|---|---|
| Component | mol % | Component | mol % | Component | mol % |
| 1-Propanol, 2-methyl- | 6.4% | Ethanol | 12.1% | 1-Propanol, 2-methyl- | 13.7% |
| Ethanol | 5.5% | Cyclopentanol, 2-methyl- | 6.1% | 1-Butanol, 2-methyl- | 7.5% |
| 1-Butanol, 2-methyl- | 4.6% | Ethanol, 2-methoxy- | 5.3% | Ethanol | 5.0% |
| 2,3-Butanediol | 4.5% | 1-Propanol | 4.9% | Cyclopentanone, 2,5-dimethyl- | 3.6% |
| Cyclopentanone, 2,5-dimethyl- | 4.0% | 2-Butanol | 4.4% | 2-Butanol | 3.5% |
| 1-Propanol | 4.0% | Cyclopentanol | 4.4% | 1-Propanol | 3.2% |
| Cyclopentanol, 2-methyl-, cis- | 3.9% | 1-Propanol, 2-methyl- | 3.7% | 2-Butanol, 3-methyl | 2.9% |
| Ethanol, 2-methoxy- | 3.2% | Isopropyl alcohol | 3.4% | 2-Butanol, 3-methoxy- | 2.6% |
| 2,3-Butanediol | 2.7% | Cyclohexanol | 3.1% | Cyclopentanol, 2-methyl- | 2.4% |
| Butanoic acid, methyl ester | 2.4% | 2-pentanol | 2.8% | 1-Pentanol, 2-methyl- | 2.3% |
| 2-Butanol | 2.3% | Acetic acid, methyl ester | 2.6% | 2-propanol | 2.3% |
| Furan, 2,5-dimethyl- | 2.2% | 1-Pentanol | 2.3% | 3-Pentanol, 2-methyl- | 2.1% |
| 2-Butanol, 1-methoxy- | 2.2% | Tetrahydrofuran, 2-propyl- | 2.1% | Ethanol, 2-methoxy | 1.9% |
| 2-Propanol | 1.9% | 1-Propanol, 3-[3-(1-methylethoxy)propoxy]- | 2.1% | 1-Butanol, 2,3-dimethyl- | 1.8% |
| 1-Pentanol | 1.9% | 1-Propanol, 2-methoxy- | 1.9% | Acetic acid, methyl ester | 1.6% |
| 3-Pentanol, 2-methyl- | 1.8% | 1-Butanol | 1.8% | Cyclopentanone, 2-methyl- | 1.6% |
| Butanoic acid, 4-methoxy-, methyl ester | 1.7% | 1-Butanol, 2-methyl- | 1.8% | Methyl propionate | 1.4% |
| Cyclopentanone, 2-methyl- | 1.7% | Methyl propionate | 1.8% | 3-Hexanol | 1.3% |
| 1-Butanol | 1.7% | Ethane, 1-ethoxy-1-methoxy- | 1.8% | Cyclopentanone, 2,5-dimethyl- | 1.3% |
| Cyclopentanone, 2,5-dimethyl- | 1.5% | Propylene Glycol | 1.7% | 1 Propanol, 2-methoxy | 1.2% |
| 1-Propanol, 2-methoxy- | 1.3% | Butyrolactone | 1.5% | 1-Butanol | 1.1% |
| Furan, 2-methyl- | 1.3% | Cyclohexanol, 2-methyl-, trans- | 1.3% | 1-Pentanol | 1.1% |
| Acetic acid, methoxy-, methyl ester | 1.0% | Methyl valerate | 1.2% | 2-Butanol, 1-methoxy | 1.0% |
| Butyrolactone | 0.9% | 2-Butanol, 3-methyl- | 0.9% | Furan, 2-methyl- | 1.0% |
| 1,2-Cyclohexanediol, trans- | 0.8% | 1-Pentanol, 2-methyl- | 0.9% | 2-Pentanol, 3-methyl | 1.0% |
| Propanoic acid, 2-hydroxy-, methyl ester | 0.8% | 1,2-Ethanediol | 0.8% | Butanoic acid, 2-ethyl-, methyl ester | 0.7% |
| Acetic acid, methyl ester | 0.6% | Butanoic acid, methyl ester | 0.7% | Butanoic acid, 2-methyl-, methyl ester | 0.6% |
| Pentanoic acid, 5-methoxy-, methyl ester | 0.6% | 2-Pentanol, 4-methyl- | 0.7% | 3-Pentanone, 2-methyl | 0.5% |
| 1-Propoxypropan-2-yl nonanoate | 0.5% | 1-Hexanol | 0.7% | 3-Hexanol, 2-methyl | 0.4% |
| Methyl valerate | 0.5% | 2-Propanol, 1-methoxy- | 0.7% | Pentanoic acid, 2-methyl-, methyl ester | 0.3% |
| Acetoin | 0.5% | Furan, 3-methyl- | 0.7% | Cyclohexanol, 2,6-dimethyl- | 0.3% |
| 2-Propanol, 1-methoxy | 0.4% | 1,2-Cyclohexanediol | 0.6% | Butanoic acid, methyl ester | 0.3% |
| Propylene glycol | 0.4% | Cyclopentanemethanol | 0.6% | Methyl valerate | 0.2% |
| Pentanedioic acid, 2-methyl-, dimethyl ester | 0.4% | 3-Pentanol, 2-methyl- | 0.6% | 2-Hexanol | 0.2% |
| Hexanedioic acid, dimethyl ester | 0.3% | Ethanedioic acid, dimethyl ester | 0.5% | 3-Hexanol, 4-methyl- | 0.2% |
| Pentanedioic acid, dimethyl ester | 0.3% | Formic acid, propyl ester | 0.5% | Hexanoic acid, methyl ester | 0.1% |

TABLE 4-continued

SCM-DHDO liquid product composition by CuMAlO$_x$ in batch.

| CuMgAlO$_x$ | | CuZrAlO$_x$ | | CuCeAlO$_x$ | |
|---|---|---|---|---|---|
| Component | mol % | Component | mol % | Component | mol % |
| Methyl propionate | 0.3% | 2-Butanol, 1-methoxy- | 0.5% | Unidentified | 27.6% |
| 1-Butanol, 2,3-dimethyl | 0.2% | Hexanoic acid, methyl ester | 0.3% | | |
| 2-Methoxy-3-methyl-butyric acid, methyl ester | 0.1% | Cyclopentanone | 0.3% | | |
| Hexanoic acid, methyl ester | 0.1% | Pentanedioic acid, dimethyl ester | 0.2% | | |
| Phenol, 2-methoxy-4-propyl- | 0.1% | 2,4-Dimethylcyclopentanol | 0.2% | | |
| 1,2-Dimethoxy-4-n-propylbenzene | 0.1% | Unidentified | 15.5% | | |
| Furan, 2-(methoxymethyl)- | 0.1% | | | | |
| Eicosane | 0.1% | | | | |
| 3-tert-Butyl-4-hydroxyanisole | 0.1% | | | | |
| 1-butanol, 3-methyl | 0.1% | | | | |
| Unidentified | 27.9% | | | | |

Overall, CuCeAlO$_x$ exhibited the highest SCM-DHDO activity and selectivity to the more energy dense C$_4$-C$_7$ alcohols (than bioethanol). The catalyst was down-selected for further performance testing in a semi-continuous SCM-DHDO reactor.

Figure 20A:
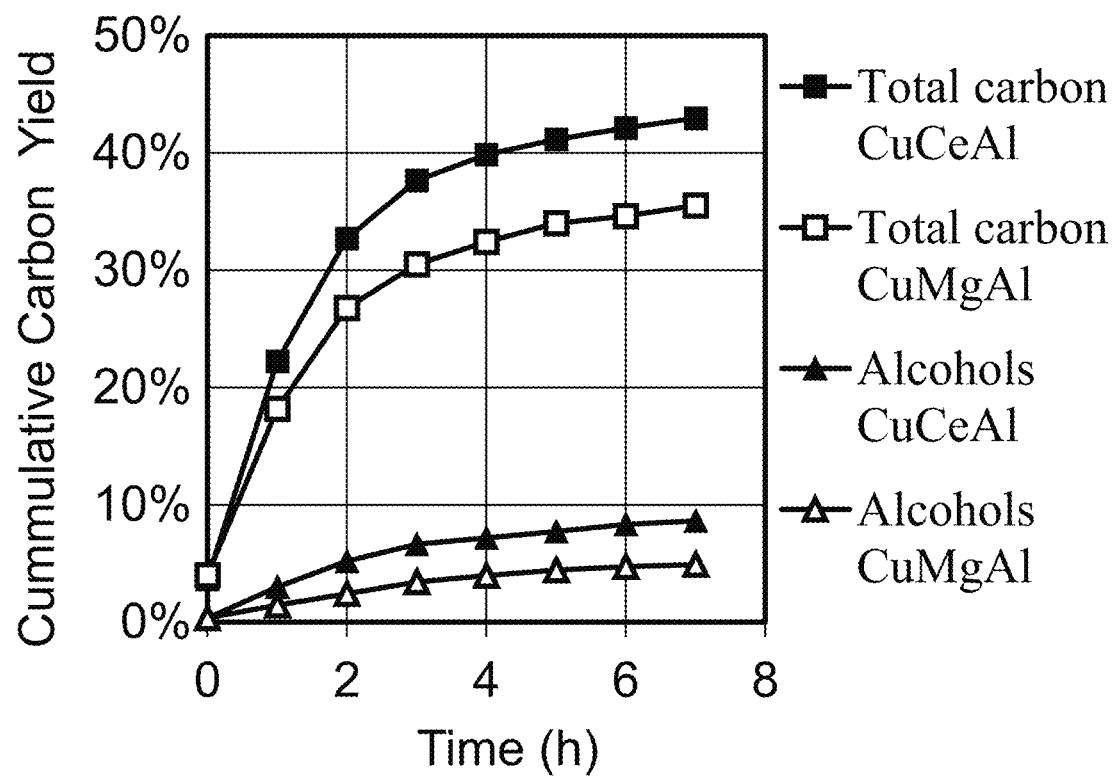
FIG. 20A illustrates cumulative total carbon and total alcohol carbon yield data from semi-continuous dual-bed SCM-DHDO reaction for 0.63 g reduced $CuCeAlO_x$ and 0.2 g reduced $CuMgAlO_x$, 300° C., 3000 psig, 100 mL/min $N_2$ and the following additional reaction conditions: ¼ in ID reactor tube, 1 g delignified biomass, 0.18 mL methanol/min methanol; step 1: 10 g delignified hybrid poplar, 1.8 mL/min methanol in 1 in ID reactor tube; step 2: 0.18 mL/min solvolyzed biomass, 0.634 g reduced $CuCeAlO_x$, 300° C., 3000 psig, 100 mL/min $N_2$, in ¼ in ID reactor tube.
Figure 20B:
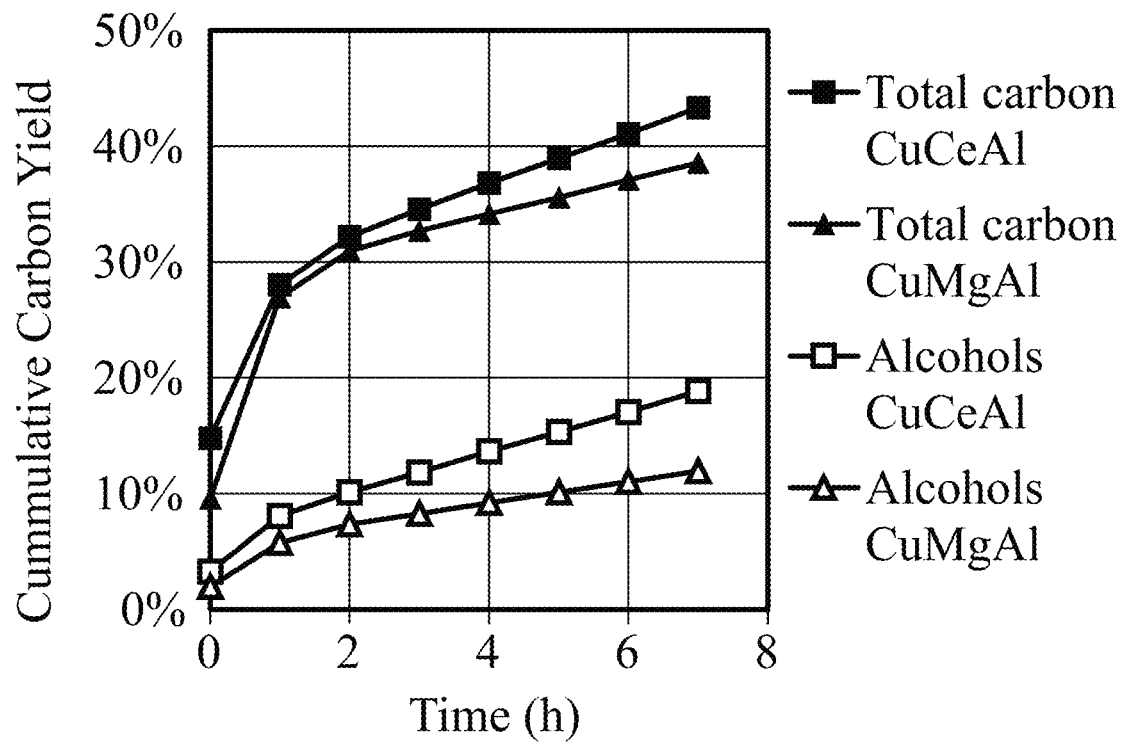
FIG. 20B illustrates cumulative total carbon and total alcohol carbon yield data from semi-continuous dual-bed SCM-DHDO reaction for 0.63 g reduced $CuCeAlO_x$ and 0.2 g reduced $CuMgAlO_x$, 300° C., 3000 psig, 100 mL/min $N_2$ and the following additional reaction conditions: 1 in ID reactor tube, 5 g delignified hybrid poplar, 0.9 mL methanol/min; step 1: 10 g delignified hybrid poplar, 1.8 mL/min methanol in 1 in ID reactor tube; step 2: 0.18 mL/min solvolyzed biomass, 0.634 g reduced $CuCeAlO_x$, 300° C., 3000 psig, 100 mL/min $N_2$, in ¼ in ID reactor tube.

Catalyst performance was evaluated in a continuous flow condition for the down-selected CuCeAlO$_x$ and the baseline CuMgAlO$_x$, using a dual-bed semi-continuous reactor (see FIGS. 20A and 20B). Under flow conditions, CuCeAlO$_x$ still displayed higher SCM-DHDO activity than CuMgAlO$_x$ with up to a 75% increase in light alcohol yield. Comparable total carbon and alcohol yields were demonstrated at about 1 g and about 5 g of delignified biomass with constant biomass loading in methanol (about 1.5 wt %) and WHSV (g MeOH (g catalyst h)$^{-1}$). Lower SCM-DHDO activity was observed in flow relative to batch for both catalysts. Specifically, total carbon yield reduced up to 58% while alcohol selectivity also lowered up to 22% when moving from batch to flow using the same amount of biomass and catalyst. Major oxygenate products shifted from alcohols in batch to esters in flow (See FIGS. 21A, 21B, 21C, and 21D) for detailed product compositions).

Without wishing to be bound by theory, the following hypothesis is proposed: (1) the initially more concentrated solvolyzed biomass streams rapidly deactivated the catalysts, and 2) diffusion limitation of sugar oligomers lowered the observed rate of C—C bond cleavage to light oxygenates. Biomass-derived oligosaccharides, whose average diameter can be from 1.03 nm for disaccharides up to hundreds of nanometers can cause catalyst pore diffusion limitation, depending on the degree of polymerization. The solvolyzed sugars molecules were likely much larger in flow, where solvolysis and catalysis were decoupled, relative to in batch, where acid sites on the catalysts' external surfaces may facilitate depolymerization to smaller oligomers to enter the pores for further reactions.

Figure 20C:
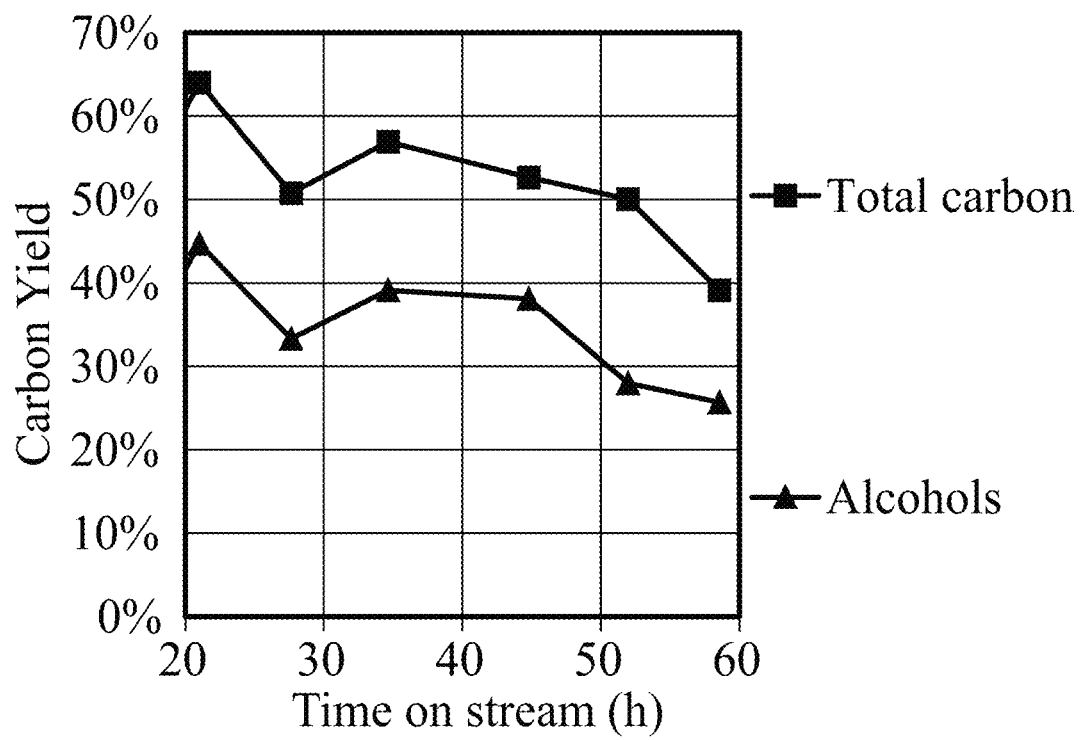
FIG. 20C illustrates total carbon yield and alcohol carbon yield with time on stream in a two-step flow reactor, according to some embodiments of the present disclosure. Reaction conditions: step 1: 10 g delignified hybrid poplar, 1.8 mL/min methanol in 1 in ID reactor tube; step 2: 0.18 mL/min solvolyzed biomass, 0.634 g reduced $CuCeAlO_x$, 300° C., 3000 psig, 100 mL/min $N_2$, in ¼ in ID reactor tube.
Figure 21A:
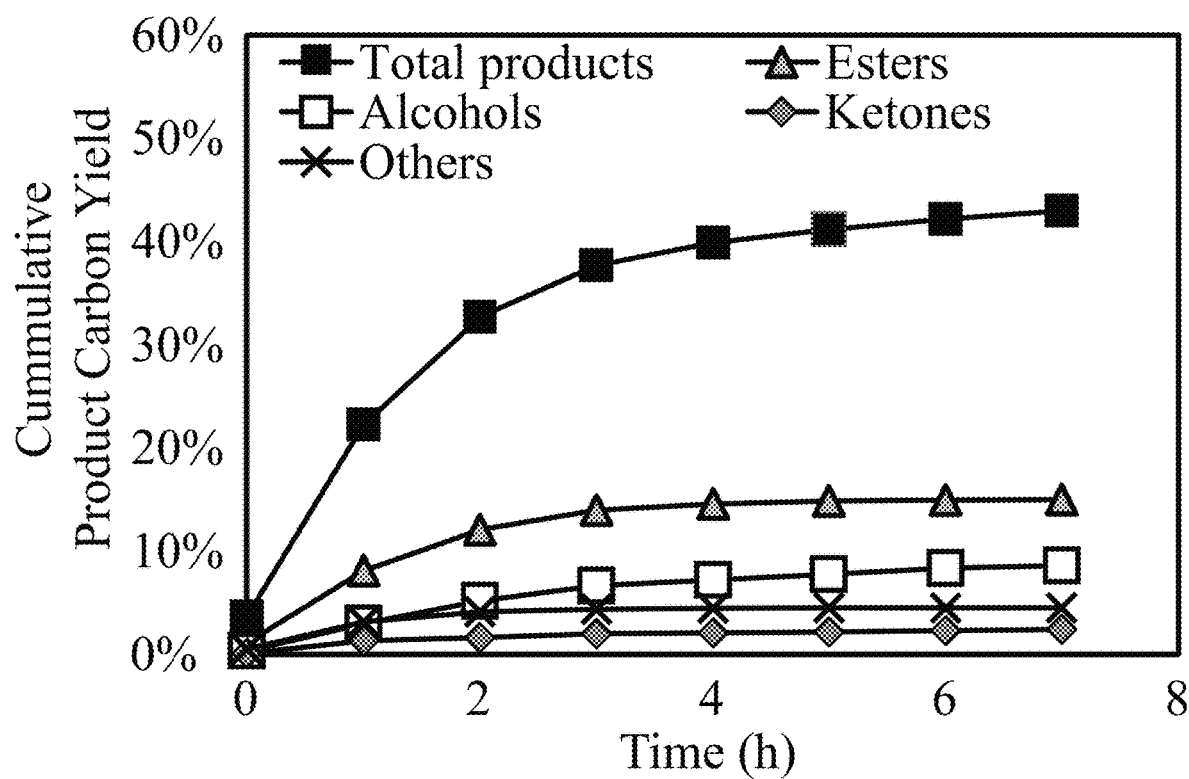
FIG. 21A illustrates cumulative carbon yield data from dual-bed semi-continuous SCM-DHDO reaction in ¼ in reactor tube for $CuCeAlO_x$, according to some embodiments of the present disclosure. Reaction condition: 1 g delignified hybrid poplar, reduced $CuMAlO_x$, 3.8 wt % Cu, 100 mL/min $N_2$, 300° C., 3000 psig.
Figure 21B:
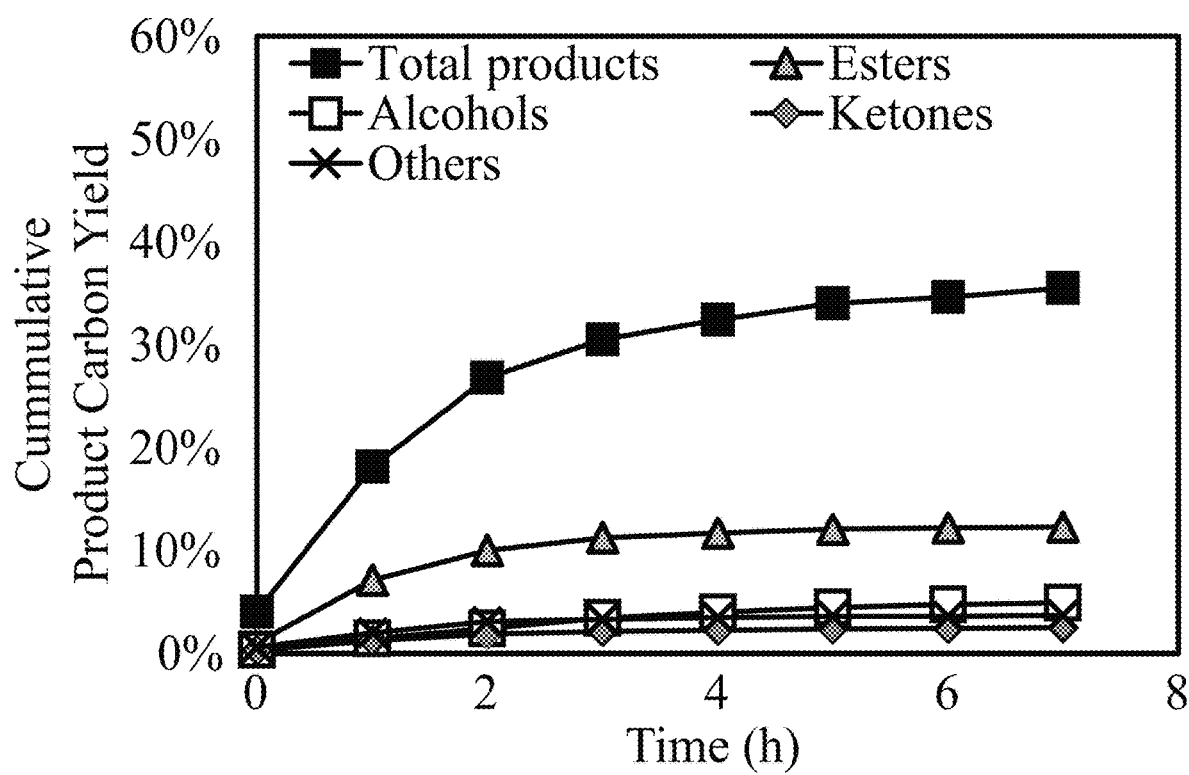
FIG. 21B illustrates cumulative carbon yield data from dual-bed semi-continuous SCM-DHDO reaction in ¼ in reactor tube for $CuMgAlO_x$, according to some embodiments of the present disclosure. Reaction condition: 1 g delignified hybrid poplar, reduced $CuMAlO_x$, 3.8 wt % Cu, 100 mL/min $N_2$, 300° C., 3000 psig.
Figure 21C:
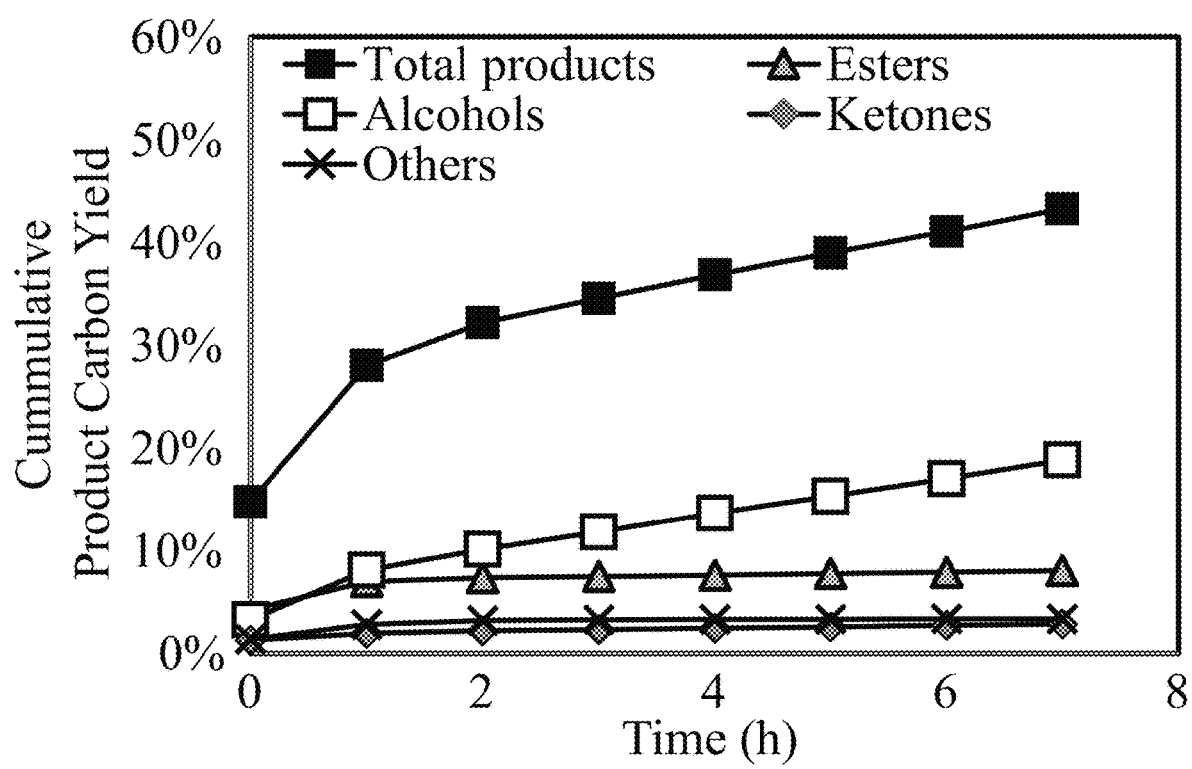
FIG. 21C illustrates cumulative carbon yield data from a dual-bed semi-continuous SCM-DHDO reaction in 1 in reactor tube for $CuCeAlO_x$, according to some embodiments of the present disclosure. Reaction condition: 5 g delignified hybrid poplar, biomass C: Cu molar ratio=63:1, 0.9 mL MeOH/min, 100 mL/min $N_2$, 300° C., 3000 psig.
Figure 21D:
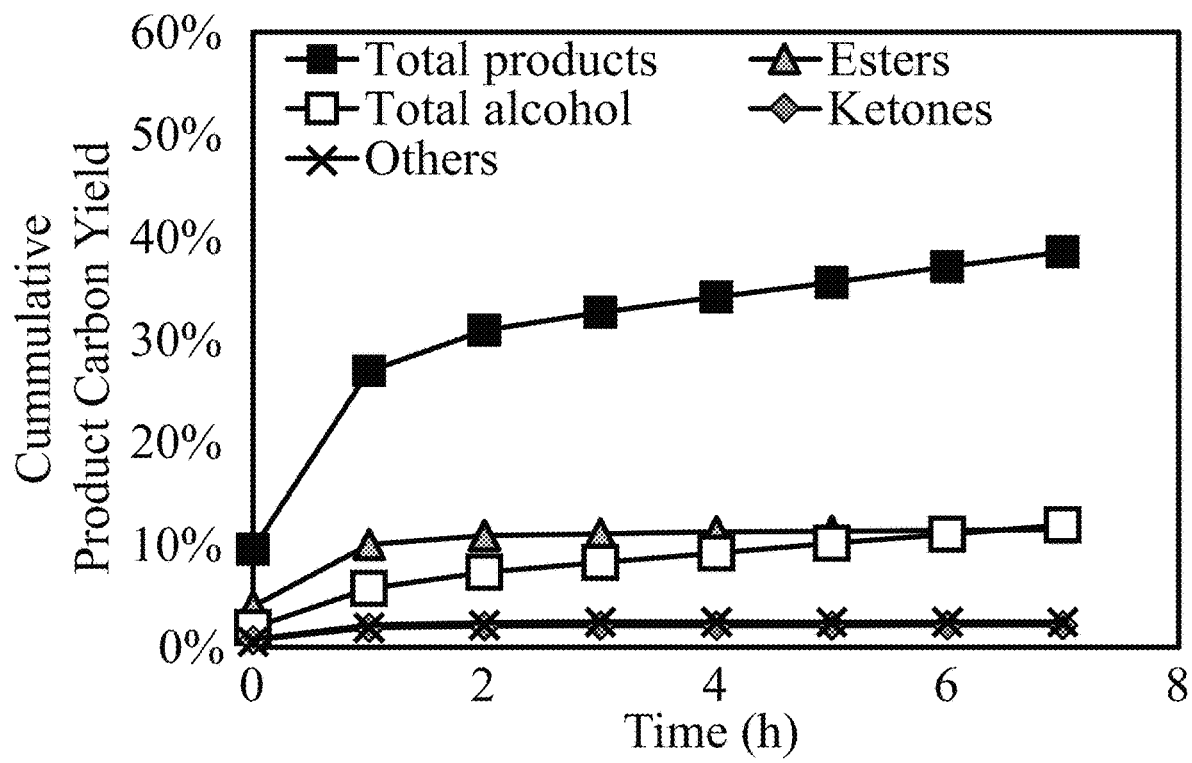
FIG. 21D illustrates cumulative carbon yield data from a dual-bed semi-continuous SCM-DHDO reaction in 1 in reactor tube for $CuMgAlO_x$, according to some embodiments of the present disclosure. Reaction condition: 5 g delignified hybrid poplar, biomass C: Cu molar ratio=63:1, 0.9 mL MeOH/min, 100 mL/min $N_2$, 300° C., 3000 psig.

Therefore, a two-step solvolysis/catalysis flow reactor was evaluated to mitigate the rapid catalyst deactivation. Here, the solvolyzed biomass in methanol was first collected before continuously fed into a CuCeAlO$_x$ catalyst bed in a second step over about a 60-hour period on stream (TOS). After an induction period, 66% total carbon yield and 44% alcohol yield were observed, which decreased to 40% and 23% respectively at 60 hours TOS (see FIG. 20C). Cumulatively, about a 58% increase in alcohol yield was observed for the two-step flow reaction relative to the one-step flow with comparable biomass loading and WHSV, supporting highly concentrated biomass as one of the causes for catalyst deactivation.

Three possible catalyst deactivation modes were assessed by characterizing the spent CuMgAlO$_x$ and CuCeAlO$_x$: (1) carbonaceous deposit (coking) by undesired C—C and C—O coupling reactions, (2) thermal sintering commonly known for Cu sites due to their high mobility at elevated temperatures, leading to agglomeration, and (3) poisoning by inorganic impurities in the raw biomass.

Figure 22A:
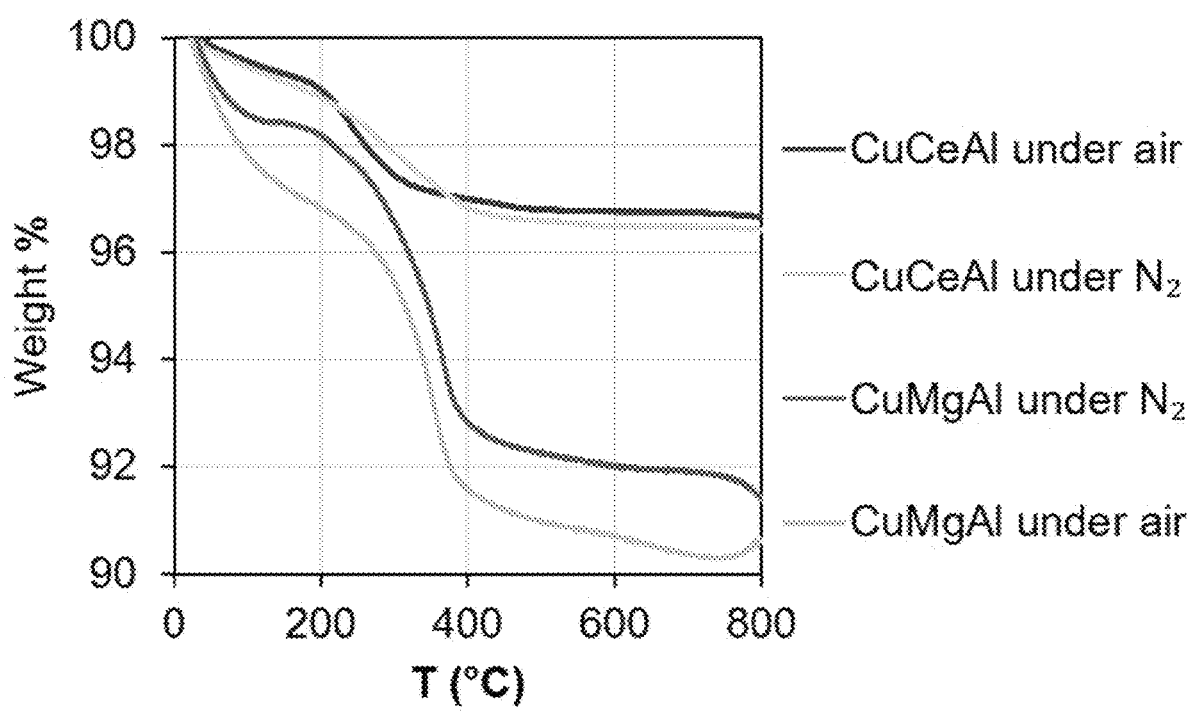
FIG. 22A illustrates TGA profiles of spent $CuCeAlO_x$ and $CuMgAlO_x$ after the semi-continues flow reaction, according to some embodiments of the present disclosure. Reaction condition: 1 g delignified hybrid poplar, 3.8 wt % Cu loading, 0.18 mL/min methanol, 100 mL/min $N_2$, 300° C., 3000 psig, catalysts were initially diluted with inert silica at 1:1 inert to catalyst volume ratio to prepare the catalyst bed. Weight loss during TGA may be attributed to the Cu-based oxides.

To investigate deactivation by coke formation, TGA and CHN analyses were conducted on the spent catalysts after the semi-continuous reactions and showed minimal carbonaceous content (see FIG. 22A). The most significant weigh loss (about 2% for CuCeAlO$_x$ and about 6% for CuMgAlO$_x$) occurred in a low temperature range (200° C.<T<400° C.), which indicated that most weigh loss was due to chemisorbed intermediates and not carbon deposits. This finding is supported by the similar TGA profiles under air and N$_2$. Comparable weight loss (between about 0.54 and about 0.68 g/g Cu) carbon content (between about 0.07 and about 0.12 g/g Cu) were observed for the spent catalyst when normalizing with Cu content. The marginal amount of coking could be partly due to Cu's low tendency to stabilize carbonium intermediates, which give rises to possible coke precursors. In addition, the relatively weak acidity/basicity of the catalysts, as well as low concentration of reactive lignin-derived aromatics, might mitigate C—C formations to heavy carbon deposits. Overall coking is likely not a major concern for the Cu-based oxide catalyst deactivation at the tested conditions.

Figure 22B:
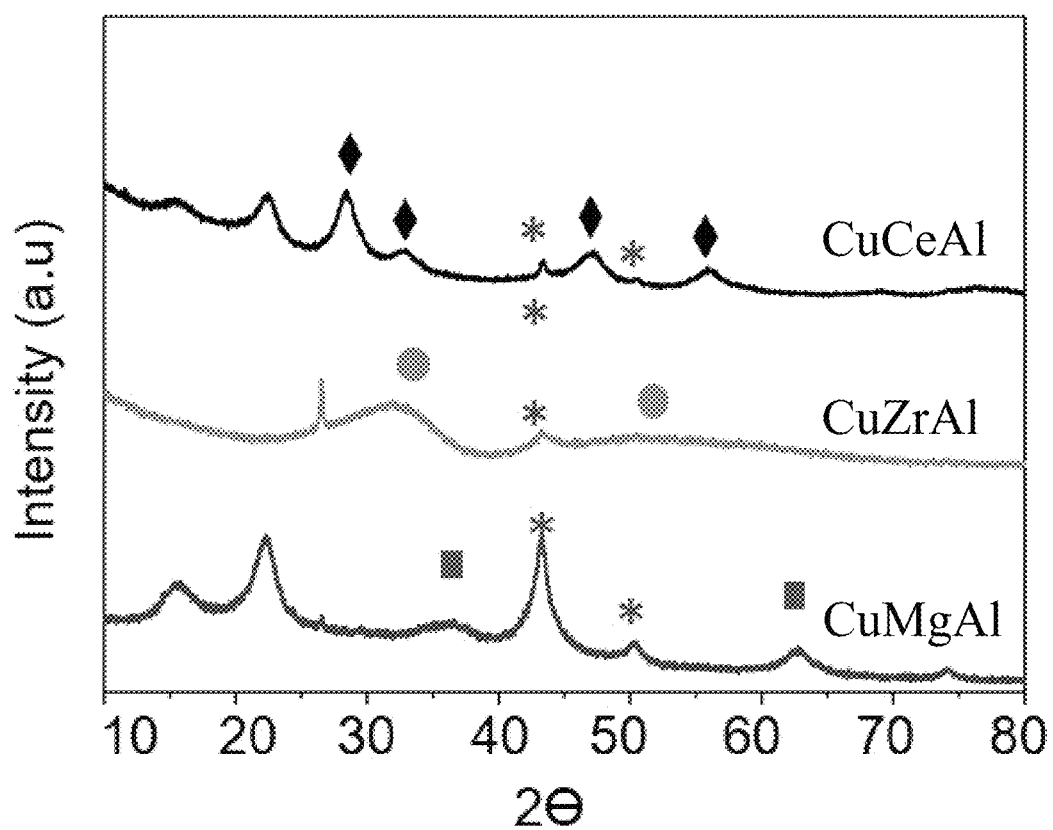
FIG. 22B illustrates XRD of the spent Cu-mixed oxide catalysts after batch reaction, according to some embodiments of the present disclosure. ■: MgO, ●: $ZrO_2$, ♦: $CeO_2$, *: Cu. Batch reaction condition: 1 g delignified hybrid poplar, reduced $CuMAlO_x$, biomass carbon:Cu molar ratio=63:1, 30 mL methanol, 300° C., 250 psi $N_2$, 2 h (not including 70 mins of heat-up time).
Figure 22C:
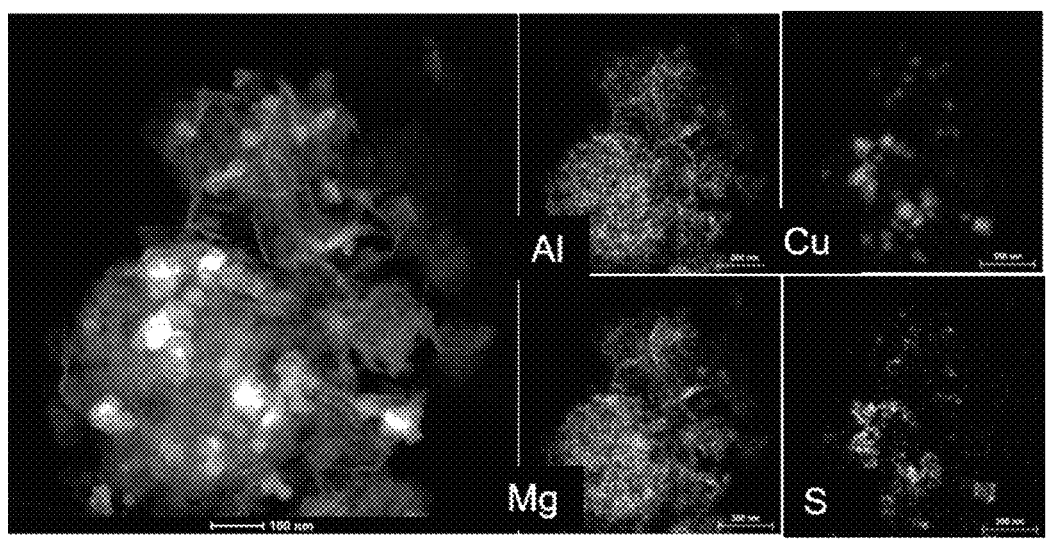
FIG. 22C illustrates STEM images with elemental mapping after SCM-DHDO batch reaction of the spent $CuMgAlO_x$, according to some embodiments of the present disclosure. Batch reaction condition as listed for FIG. 22B.
Figure 22D:
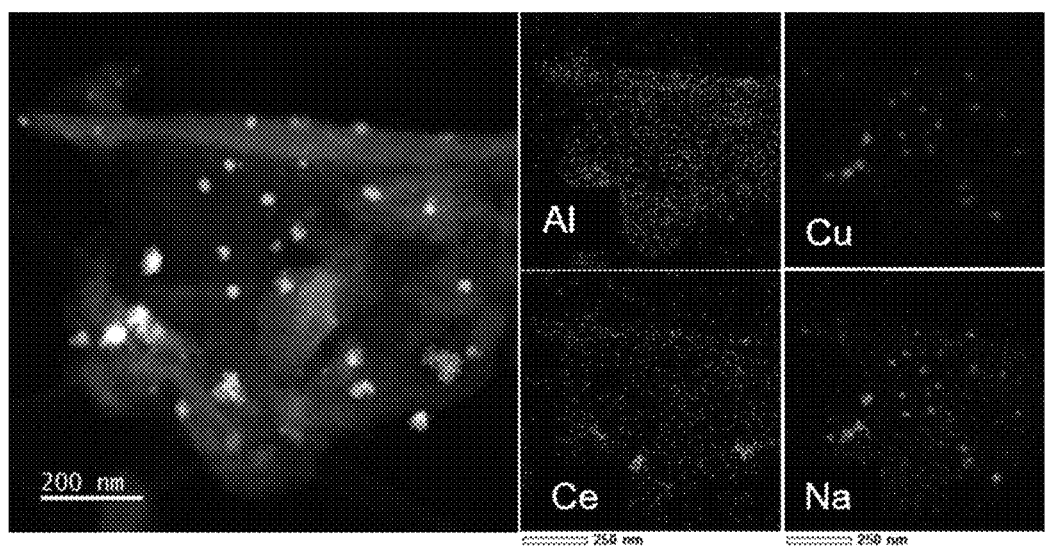
FIG. 22D illustrates STEM images with elemental mapping after SCM-DHDO batch reaction of $CuCeAlO_x$, according to some embodiments of the present disclosure. Batch reaction condition as listed for FIG. 22B.

Thermal sintering of Cu nanoparticles was observed by XRD (see FIG. 22B) and STEM-EDS (see FIGS. 22C and 22D) for both spent catalysts after batch reactions. A group of diffraction peaks appear at about 43.8°, 51.05° and 74.86°, corresponding to (111), (200), and (220) planar of Cu in the XRD patterns of the spent catalysts. Although some small Cu nanoparticles remained, other Cu particles grew from <5 nm in fresh catalysts to a range between about 75 nm and about 85 nm as determined by Scherrer estimation and confirmed by STEM. This suggests that loss in active Cu metal surface area by thermal agglomeration is likely a deactivation mechanism.

Lastly, the effect of biomass impurities (e.g., S, P, alkali) on catalyst structure was examined by elemental mapping of the spent catalysts. STEM-EDS images showed that in CuMgAlO$_x$, S concentrated where Cu nanoparticles are (see FIGS. 22C and 22D). This indicates Cu—S complex formation that might have poisoned and reduced the reactivity of the Cu sites. In contrast, S scattered on CuCeAlO$_x$ surface rather than on Cu particles, likely due to the presence of CeO$_2$. CeO$_2$ doping in metal-supported catalysts has been shown to prevent the active metal sites from sulfur poisoning by forming Ce$_2$O$_2$S complex. Instead of S, Na was found where the Cu particles are for CuCeAlO$_x$, which can also impact activity of the Cu sites. Therefore, while biogenic impurities appeared to deactivate both catalysts, the specific poisoning elements depend on catalyst composition and must be accounted for when evaluating mitigation strategies. Therefore, short-term stability of the CuMAlO$_x$ was attributed to agglomeration of Cu metal site and biogenic poisoning under the reaction conditions screened here.

Fuel properties of the SCM-DHDO product mixture were evaluated against typical light-duty fuel metrics, using both fuel surrogates and the real reaction products using CuCeAlO$_x$. The evaluation of fuel surrogates serves as guidance for the real SCM-DHDO conversion and separation processes towards production of a desirable fuel product. To do this, a neat base surrogate was prepared from the top twenty-five most concentrated SCM-DHDO light oxygenates. Detailed compositions of this and other modified surrogates are listed in Table 5. This surrogate was used to determine anticipated fuel properties of the neat product and investigate the fuel impact of methanol solvent residues after distillation. These surrogates were evaluated for their characteristics upon blending at 10 vol % into a base gasoline RBOB (reformulated blendstock for oxygenate blending). Fuel properties of the neat and blended surrogates were measured, then evaluated for their merit as light-duty fuels This evaluation was done by evaluating both the impact of blending on the base RBOB, as well as comparison to ethanol against the neat surrogates and E10 (in RBOB) against the blended surrogates (see Table 6). E10 is used here as a basis of comparison due to its widespread use in the USA as a bioderived drop-in gasoline blend.

TABLE 5

Detailed composition of the SCM-DHDO surrogate (tope 25 components) and final SCM-DHDO biofuel product from delignified hybrid poplar using reduced CuCeAlO$_x$ in batch after purification, excluded 25% methanol.

| Surrogate: Top 25 | | SCM-DHDO Final Product | |
|---|---|---|---|
| Component | Mol % | Component | Mol % |
| 1-Propanol, 2-methyl- | 21.0% | 1-Propanol, 2-methyl- | 17.3% |
| ethanol | 15.4% | 1-Butanol, 2-methyl- | 8.5% |
| 3-methoxy-1-butanol | 9.2% | 1-Propanol | 3.5% |
| 1-propanol | 6.5% | Cyclopentanone, 2,5-dimethyl- | 6.9% |
| 2-butanol | 5.3% | 3-Pentanol, 2-methyl- | 5.9% |
| 2-propanol | 4.7% | 2-Butanol | 3.7% |
| 2-methoxy ethanol | 3.9% | 3-Pentanol, 2,4-dimethyl- | 5.0% |
| 3-methyl-2-butanol | 3.5% | (R)-(−)-3-Methyl-2-butanol | 3.2% |
| methyl acetate | 3.4% | 2-Butanol, 3-methoxy- | 2.8% |
| 1-methoxy-2-propanol | 3.2% | Ethanol, 2-methoxy- | 1.6% |
| cyclopentanone | 3.2% | Cyclopentanone, 2-methyl- | 3.2% |
| 3-methyl-cyclopentanol | 2.5% | Cyclopentane, 1,1-dimethyl- | 3.4% |
| 2-methyl-1-pentanol | 2.4% | Cyclopentanol, 2-methyl-, cis- | 2.7% |
| methyl propionate | 2.2% | 1-Butanol, 2,3-dimethyl- | 2.5% |
| 2-methyl-3-pentanol | 2.1% | Cyclopentanone, 2,5-dimethyl- | 2.9% |
| methyl butyrate | 1.8% | Cyclohexanol, 1-methyl- | 2.9% |
| 2-methyl cyclopentanone | 1.7% | 3-Pentanone, 2,4-dimethyl- | 2.4% |
| 1-butanol | 1.7% | 2-Methoxy-3-methyl-butyric acid, methyl ester | 2.3% |
| 3-hexanol | 1.4% | 2,3-Butanediol | 1.3% |
| 1-pentanol | 1.3% | 1-Propanol, 2-methoxy- | 1.1% |
| 2-methyl-3-pentanone | 1.3% | 2 butanol, 3-methoxy | 1.1% |
| 2-methyl furan | 1.3% | ethanol | 0.4% |
| Methyl 2-methylbutyrate | 0.3% | 2-propanol | 0.6% |
| 2-methyl-1-butanol | 0.2% | Acetoin | 0.8% |
| methyl valerate | 0.1% | 1-Butanol | 0.8% |
| | | Propanoic acid, 2-methoxy-, methyl ester | 0.9% |
| | | 2-Butanol, 3-methoxy- | 0.7% |
| | | 3-Hexanol, 2-methyl- | 0.9% |
| | | Butyric acid, 2-hydroxy-3-methyl-, methyl ester | 0.7% |
| | | 3-Pentanone, 2-methyl- | 0.7% |
| | | Propane, 1-ethoxy-2-methyl- | 0.5% |
| | | Formic acid, 1-methylpropyl ester | 0.3% |
| | | Oxirane, 2-methyl-3-propyl-, cis- | 0.3% |
| | | Methyl propionate | 0.2% |
| | | 2-Butanol, 1-methoxy- | 0.3% |
| | | Butanoic acid, 2-methyl-, methyl ester | 0.3% |
| | | 2-Propanol, 1-methoxy- | 0.2% |
| | | Furan, 2-methyl- | 0.1% |
| | | Butyrolactone | 0.04% |
| | | Unidentified | 7.0% |

TABLE 6

Fuel properties of neat and blend SCM-DHDO surrogates and the final biofuel product, ethanol and blend ethanol and RBOB

| Light Duty Fuel Property | SCM-DHDO Surrogate | Ethanol | RBOB[a] | Ethanol Blended at 10 vol % | SCM-DHDO Surrogate Blended at 10 vol % | SCM-DHDO Surrogate with 25% MeOH Blended at 10 vol % | Bio-Derived SCM-DHDO Blended at 10 vol %* |
|---|---|---|---|---|---|---|---|
| LHV (MJ/kg) | 41.22 | 26.84 | 42.83 | 38.8 | 41.75 | 41.46 | 41.22 |
| Density at 15° C. (g/mL) | 0.763 | 0.793 | 0.744 | 0.73 | 0.765 | 0.764 | 0.763 |
| RON | 89.4 | 109 | 87.5 | 92.7 | 87.5 | 88.6 | 89.4 |
| MON | 82.6 | 90.0 | 80.6 | 83.5 | 81.6 | 82.3 | 82.6 |
| AKI | 86.0 | 99.5 | 84.1 | 88.1 | 84.6 | 85.5 | 86.0 |
| RVP (psi) | 6.91 | 2.6 | 5.28 | 6.40 | ND | 6.12 | 6.91 |
| HoV (kJ/kg) | 422 | 919 | 359 | 418 | 363 | 384 | 422 |
| Cloud Pt. (° C.) | <−75 | <−114 | <−70 | <−40 | <−75 | <−75 | <−75 |
| T90 (° C.) | 172 | 78.4 (BP) | 171 | 168 | 184 | 173 | 172 |
| Ox. Stability (min) | 58 | NA | 93 | 94 | 58 | 65 | 37 |

Energy densities (reported using lower heating value, LHV) of the SCM-DHDO surrogates were comparable to the gasoline RBOB and higher than that of the E10. The 54% increase in LHV of the neat surrogate (41.22 MJ/kg) relative to ethanol (26.84 MJ/kg) was attributed to the high selectivity of the larger $C_4$-$C_7$ alcohols by $CuCeAlO_x$. Energy density of the surrogates appeared to increase linearly with vol % blend level in the RBOB, resulting in the LHV of the 10 vol % surrogate blend (41.46 MJ/kg) being increased relative to E10 (38.8 MJ/kg). In addition, the minimal change in LHV of the blended surrogates with or without 25% methanol, indicated that this level of methanol residue (~2.5% overall) does not significantly impact the fuel energy density. The high energy density maintained by the surrogates suggests SCM-DHDO products do not reduce fuel economy (miles per gallon) of the base gasoline as is the case with E10. This is particularly impactful considering the carbon reduction and emissions benefits of eventually achieving higher renewable oxygenate blend levels than the current 10% bioethanol convention.

The surrogates and blends exhibited lower knock resistance (anti-knock index, AKI), than their ethanol counterparts. This is because ethanol itself has a high AKI and is known (in addition to methanol) to provide a nonlinear increase in AKI with increasing blend level in gasolines, though with diminishing returns after 30 vol % augmented by the simultaneous decrease in energy density. The surrogates and blends comprise primarily larger alcohols which do not provide these boosting effects. Additionally, AKI typically decreases with increasing alcohol chain length (for example AKI of 1-butanol, 1-pentanol, and 1-hexanol is respectively 92, 76 and 67). Although lower than AKI of E10 (88.1), AKI of the blend surrogate (84.6) was still greater than that of the base fuel RBOB (84.1) and was even enhanced in the presence of methanol (85.5). This indicates that methanol residues may in fact provide the small-alcohol engine knocking resistance boost without compromising fuel energy density.

A high heat of vaporization (HoV) can also help suppress knocking, in that the spray of a high-HoV fuel in an SI cylinder can provide a charge cooling effect which prevents more reactive components of the fuel from igniting prematurely and causing knock. The surrogates exhibited ~2.1 times lower HoV than ethanol, which can be attributed to both the tendency of ethanol to synergistically increase HoV upon blending, on top of the longer-carbon (lower HoV) components of the surrogate. However, too high an HoV can result in a fuel not vaporizing readily, acting as a fuel with a high T90 (low volatility). This can suppress evaporation particularly of heavier fuel components, which can result in increased sooting propensity. This necessarily caps the blend level of ethanol in fuels and makes a good case for use of the SCM-DHDO surrogates as a safe bio-blendstock alternative.

The implications of volatility can also be seen by examination of Reid vapor pressure (RVP, vapor pressure at 100° F.), which was ~2.6 times higher in the neat surrogate than that of neat ethanol, but similar once blended into the RBOB (for the surrogate with residual methanol). These phenomena are likely due to nonlinear blending impacts of both ethanol (in RBOB) and methyl acetate (in the surrogate). The presence of highly volatile components such as methyl acetate (4.6 psia). The RVP of gasoline is capped by the EPA depending on season and climate in order to control evaporative emissions. This cap also serves to avoid the possibility of drivability issues in warmer ambient temperatures. Unlike energy density, RVP can be dominated by traces of volatile compounds and intramolecular forces between oxygenates and hydrocarbons, which can vary greatly based on the mixture composition. At the same time as maintaining some degree of volatility by including lighter components, carbon number must be low enough such that the fuel does not freeze causing low temperature drivability issues. All measured neat and blended fuels met necessary freezing or cloud point criteria.

The fuel surrogates displayed lower oxidation stability than ethanol and the base fuel RBOB, indicating lower infrastructure compatibility of the SCM-DHDO product. The observed earlier instability onset (up to 38%) may be due to the high content (9%) of 3-methoxy-1-butanol in the neat surrogate. Branched ether functionality is shown as more susceptible to oxidation than the other linear ethers or alcohols. Despite a slight improvement in stability once the surrogate included 25% methanol, this early onset behavior appeared to be governed by trace levels of highly reactive components and was not improved upon dilution in RBOB.

Fuel surrogate studies demonstrated the potential of SCM-DHDO product to increase fuel energy density due to higher content of $C_4$-$C_7$ alcohols, as well as keep RVP low and HoV metered relative to E10. Both blending into the RBOB and inclusion of methanol residues enhanced oxidation stability and anti-knock index without compromising energy density. Therefore, the 10% vol blend surrogate with 25% methanol was chosen as the target for fuel composition of the real SCM-DHDO product.

The SCM-DHDO liquid mixture was produced in batch reactions by $CuCeAlO_x$, distilled and blended 10% vol in RBOB to form the final SCM-DHDO fuel blend (see Experimental Section for details). The neat fuel fraction contained 23% methanol, with the balance comprising light oxygenates whose composition closely matched with the neat surrogate. (see Table 5 above for detailed composition). Measured fuel properties of the SCM-DHDO fuel blend were comparable to those of the target blend surrogate, with the exception of oxidative stability. The significantly shorter onset time (37 min) relative to the target blend (65 min) suggested higher level of reactive compounds (e.g., furans, aromatics, carbonyls) that were not fully captured in the surrogate. This oxidative stability may be improved through the catalytic conversion to enhance hydrogenation and reduce the composition of these unsaturated components.

Whether or not a reactant or product described herein is "bioderived" may be determined by analytical methods. Using radiocarbon and isotope ratio mass spectrometry analysis, the biobased content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pMC value obtained correlates directly to the amount of biomass material present in the sample. Thus, ASTM-D866 may be used to validate that the compositions described herein are and/or are not derived from renewable sources.

EXPERIMENTAL

Catalyst synthesis: The copper-based mixed oxide catalysts were synthesized using co-precipitation method. The desired catalyst formula is $CuMAlO_x$ where M is Mg, Zn, Cr, Zr or Ce, (Cu+M)/Al molar ratio=3:1, and Cu:M molar ratio=1:4. The nitrate and chloride precursor salts, including $MgCl_2 \cdot 6H_2O$, $AlCl_3 \cdot 6H_2O$, $ZnCl_2$, $Ce(NO_3)_3 \cdot 6H_2O$, $Cr(NO_3)_3 \cdot 9H_2O$, $ZrO(NO_3)_2 \cdot xH_2O$, and $Cu(NO_3)_2 \cdot 3H_2O$, and $Na_2CO_3$ were purchased from Sigma Aldrich. NaOH was purchased from Fisher Scientific. In a typical synthesis, 75 mL of aqueous solution containing $Cu(NO_3)_2 \cdot 3H_2O$, $AlCl_3 \cdot 6H_2O$ and metal M nitrate or chloride salt was added dropwise into a beaker containing 93.75 mL aqueous solution of $Na_2CO_3$ (0.0125 mol), stirred at 60° C. The pH was maintained at 9.5-10 by adding 1M NaOH solution. The resulting solution was aged at 60° C., pH 10 for 24 h, followed by vacuum filtering and washing with deionized water. The filtered solid was dried overnight at 110° C., sieved to 75-125 μm particle size, then calcined at 460° C. in air for 24 h with 5° C./min ramping rate. The calcined catalyst was reduced in 10% $H_2/N_2$ at 350° C. for 5 h with 5° C./min ramping rate. After reduction, the catalyst was passivated with 1% $O_2/N_2$ for 1 h at 30° C., purged with $N_2$ then immediately transferred to the reactor vessel for catalytic activity testing.

Catalyst characterization: Catalyst BET surface area, BJH pore size and pore volume was measured by $N_2$ physisorption using Quadrasorb SI™ surface area analyzer from Quantachrome Instrument. In a typical measurement, 0.10 g of catalyst was degassed under vacuum at 200° C. for 16 hours directly before analysis. Full adsorption and desorption isotherms were recorded for each sample at 77 K. Surface area was computed using the BET method, while pore volume and pore size distribution were determined using the BJH method for the desorption isotherm branch.

Total acid density of the catalyst was measured by $NH_3$ temperature programmed desorption, using an Autochem II 2920 (Micromeritics). Approximately 0.10 g of catalyst was loaded into a quartz u-tube and supported by quartz wool. After purging the system with helium, the catalyst was pretreated by ramping to 90° C. for 0.5 hours, then 600° C. K for 2 hours in 50 $cm^3$ (STP) $min^{-1}$ helium. After cooling to 120° C., a stream of premixed 10.0% $NH_3$ (balance helium, General Air) was passed over the catalyst for 1 hour to saturate acidic sites on the catalyst surface. Following a 2-hour helium purge at 393 K to remove physiosorbed $NH_3$, the sample temperature was ramped to 873 K at 10 K $min^{-1}$ in helium carrier gas at 10 $cm^3$ (STP) $min^{-1}$, while $NH_3$ concentration in the effluent was monitored by TCD. After calibrating the TCD, the desorption peak area was used to calculate the total quantity of acid sites by assuming a 1:1 stoichiometry of $NH_3$ molecule to catalyst acid site.

Catalyst testing: A typical catalyst activity test was conducted in a 100 mL Parr batch reactor, equipped with overhead stirring. The reactor vessel, containing 1 g biomass, a fixed amount of reduced catalyst, and 30 mL HPLC grade methanol, was heated to 300° C. in a tubular furnace encloser. After a certain period, the reactor was quickly quenched down in an ice bucket, and the headspace gas, liquid products, and solid residues were collected for analysis.

Semi-continuous flow reaction was conducted in a reactor vessel tube (Parr), rated to 550° C. and 5000 psi, enclosed in a split-tube furnace (Thermcraft) rated to 550° C. In a typical experiment, the reactor vessel was packed with delignified biomass at the top, a fixed amount of reduced Cu-based mixed metal oxide catalyst at the bottom, and quartz wool and inert glass beads at both ends of biomass and catalyst beds. Methanol solvent, containing 1% n-dodecane as internal standard, was fed to the reactor system by a HPLC pump (Lab Alliance). Inert gas was introduced through a high pressure calibrated mass flow controller (Brook). Pressure in the reactor was maintained at 3000 psi by a back-pressure regulator (Swagelok). Gas flow and system pressure were controlled by valve controller. Reactor temperature was controlled and monitored via a 1/16" dual thermocouple by a power controller. Both controllers were connected to a Parr 4871 controller, which interfaced with the computer through a SpecView control software (Honeywell). The reactor vessel was heated up to 300° C. and stabilized in an hour. Gas and liquid product effluents were condensed by a chiller (Lauda WKL 230) with ethyleneglycol and water mixture (30:70) and collected in a 1-L high pressure vessel (Parr) and periodically sampled for analysis through a bottom sampling port.

Product analysis: After a reaction, the solid residues were collected, dried and weighed to determine biomass conversion. Headspace gas products were analyzed by a micro-GC (Agilent 490), containing four different columns, including a Molecular Sieve 5A (to measure helium, hydrogen, nitrogen, CO and methane), a PoraPLOT Q (to measure $CO_2$, C2-C3 hydrocarbon), a CP-Sil 5CB (to detect C4-C5 hydrocarbon), and a CP-Wax 52CB. Total run time for each column was 120 seconds. Each gas bag was injected 7 times to stabilization and the results from the last run were used for quantification. The liquid products were filtered and analyzed with a gas chromatogram (Agilent 7890A), equipped with an HP-5 column, a mass spectrometer (Agilent 5975), a Polyarc® analyzer and a flame ionization detector. Quantification of products was based on calibration of the internal standard n-dodecane and their carbon numbers.

Physisorption: Catalyst BET surface area, BJH pore size and pore volume were measured by $N_2$ physisorption using Quadrasorb SI™ surface area analyzer from Quantachrome Instrument. In a typical measurement, 0.10 g of catalyst was degassed under vacuum at 200° C. for 16 hours directly before analysis. Full adsorption and desorption isotherms were recorded for each sample at 77 K. Surface area was computed using the BET method, while pore volume and pore size distribution were determined using the BJH method for the desorption isotherm branch.

Chemisorption: Total acid and base density of the catalyst was measured by temperature programmed desorption (TPD) of $NH_3$ and $CO_2$ respectively, using an Autochem II 2920 (Micromeritics). Approximately 0.10 g of catalyst was loaded into a quartz u-tube and supported by quartz wool. After purging the system with He, the catalyst was pre-treated by ramping to 90° C. for 0.5 hours, then 600° C. K for 2 hours in 50 $cm^3$ $min^{-1}$ helium. After cooling to 120° C., a stream of premixed 10% $NH_3$/balance helium (General Air) was passed over the catalyst for 1 hour to saturate acidic sites on the catalyst surface. Following a 2-hour helium purge at 393 K to remove physiosorbed $NH_3$, the sample temperature was ramped to 873 K at 10 K $min^{-1}$ in helium carrier gas at 10 $cm^3$ $min^{-1}$, while $NH_3$ concentration in the effluent was monitored by TCD. After calibrating the TCD, the desorption peak area was used to calculate the total quantity of acid sites by assuming a 1:1 stoichiometry of $NH_3$ molecule to catalyst acid site. $CO_2$ TPD follows the same procedure with 10% $CO_2$/balance He.

ICP: The elemental content of the catalysts was analyzed via ICP-OES (Agilent 5110). Initially, approximately 25 mg of each catalyst was weighed out and dissolved in 10 mL of concentrated $HNO_3$. This mixture was heated in a Teflon vessel at 200° C. for 30 min in a microwave digestion system (CEM MARS5) operating at 1600 W. Elemental concentrations were quantified after ICP-OES analysis using the following characteristic emission peaks: 396.152 nm (Al), 418.659 nm (Ce), 327.395 nm (Cu), 279.553 nm (Mg), 213.857 nm (Zn), 343.823 nm (Zr).

XRD: Powder X-ray diffraction (XRD) patterns of the catalysts at various stages (before calcined and after calcination, reduced and post reaction) were measured by a Rigaku Ultima IV diffractometer with a Cu Kα source operating at 40 kV and 44 mA. Scans were collected in the 2θ range of 20-80 degrees at a scan rate of 4° $min^{-1}$. The crystallite sizes of Cu were calculated from XRD peak broadening using the Scherrer equation.

TGA: Thermal gravimetric analysis (TGA) on the spent catalysts was acquired on TA Instruments Q-5000 with Pt pans. In each measurement, 10-20 mg catalyst was used, and temperature ramp of 5° C./min was applied to the sample in the range of 25-850° C. under 30 mL/min air or $N_2$ flow.

CHN: Carbon and hydrogen content analysis on the spent catalyst were conducted by combustion using a LECO Series 628 Carbon/Hydrogen/Nitrogen Determinator STEM-EDS: High Resolution (HR) Scanning transmission electron microscopy (STEM) imaging and elemental mapping of the Cu-based oxides were conducted on an aberration corrected JEOL JEM-ARM200CF TEM/STEM (ARM stands for Atomic Resolution Microscope) operated at 200 kV with a unique cold field emission gun (Cold-FEG), a next generation Cs corrector (ASCOR) that compensates for higher order aberrations and energy dispersive X-ray spectroscopy (EDS) system with dual JEOL 100 $mm^2$ silicon-drift detectors (SDD) with a large solid angle of 0.98 Steradian from a detection area of 100 $mm^2$ for chemical analysis. Simultaneous bright field (BF) and HAADF-STEM images were acquired but only HAADF-STEM images are presented here. HR-STEM analysis was performed with a nominal beam current of ~25 pA and associated resolution of a nominal 0.07 nm. To avoid and/or decrease any potential electron beam damage during spectroscopy analysis but maintain high signal-to-noise ratio, the current of the electron beam was controlled and was set to ~94 pA. TEM samples were prepared by drop-cast method with the catalysts being dispersed in ethanol, sonicated and deposited onto lacey carbon-coated gold grids (SPI Supplies part no. Z3820G) to avoid additional x-rays from the Cu grid.

Fuel production and separation methods: The production of liquid oxygenates for fuel property testing was conducted in batch by the down-selected $CuCeAlO_x$ catalyst, since $CuCeAlO_x$ showed the highest alcohol yield and selectivity. The mixed oxide was synthesized in large quantity (up to 20 g) through the previously described co-precipitation method. The catalyst was used for scaled SCM-DHDO batch reaction with delignified hybrid poplar. In a typical experiment, 1 g of delignified hybrid poplar, 0.64 g of catalyst, and 30 mL of methanol were added to a 100 mL reactor vessel, which was then heated to 300° C. in a tubular furnace encloser for 2 h. The experiment was repeated until 450 mL of the final product was collected and subjected for further purification, including water removal and distillation of methanol solvent and heavy products to the desirable fuel cut.

Water removal: Water is a byproduct of dehydration reactions during SCM-DHDO processing that can cause immiscibility in the final fuel. Karl Fisher titration determined a water content of 2.8 wt % that was removed with molecular sieves 3 Å. 12.5 wt % of molecular sieves were activated, added to the liquid products and stored in a $N_2$ purged desiccator for 49 h. During this time, the saturated sieves were periodically replaced with a freshly activated batch of sieves and a sample was taken for water content measurement by Karl Fischer titration.

Distillation: After drying, the fuel was distilled using a BR Instruments® Micro-distillation column with 250 ml source flask to separate the methanol solvent and heavy products from the target fuel molecules. The fuel was then blended with RBOB base fuel for fuel property tests. The BR Instruments® Micro-distillation column was run at atmospheric pressure and heated at an initial rate of 10% and increased to 12.5% after the first few milliliters of distillate (methanol is the first component to boil off) were collected. The reflux ratio was held at 20 until the first few milliliters of distillate were collected at which point the reflux ratio was decreased to 3. The condenser circulating an 80:20 water to ethylene glycol mixture was held at 7° C. for the duration of the distillation. A Teflon band rotating 120 rpm was used in the column. The methanol fraction was collected in the distillate from room temperature up to 58.4° C. The fuel fraction was then collected from 58.5° C. up to 100° C. and required increasing the heat rate incrementally up to 40%, with the heavy product fraction left in the bottoms.

EXAMPLES

Example 1

A composition comprising: copper (Cu), aluminum (Al), oxygen, and an element (M) comprising at least one of magnesium, cerium, or a transition metal, wherein: the copper and the element are present at a first molar ratio relative to the aluminum between about 0.1:1 and about 30:1 ((Cu+M):Al), and the copper and the element are present at a second molar ratio between about 0.1:4 and about 20:1 (Cu:M).

Example 2

The composition of Example 1, wherein the second molar ratio is between about 1:1 and about 10:4 (Cu:M).

Example 3

The composition of Example 1, wherein the copper, aluminum, and the M are each incorporated into an oxide.

Example 4

The composition of Example 3, wherein the transition metal comprises at least one of zinc, zirconium, chromium, scandium, titanium, niobium, vanadium, hafnium, tungsten, or tantalum.

Example 5

The composition of Example 4, wherein M comprises at least one of magnesium, zirconium, cesium, or zinc.

Example 6

The composition of Example 1, the composition may further include a third molar ratio of a molar hydrogen ($H_2$) capacity, in moles of $H_2$ per gram of the composition ($c_1$), to a molar concentration of the Cu, in moles of Cu per gram of the composition ($c_2$), wherein the third molar ratio is between about 0.5:1 and about 10:1 ($c_1:c_2$).

Example 7

The composition of Example 6, wherein the third molar ratio is between about 1:1 and about 3.4:1.

Example 8

The composition of Example 1, further comprising an average pore size between about 0.1 nm and about 60 nm.

Example 9

The composition of Example 8, wherein the average pore size is between about 1.0 nm and about 10 nm.

Example 10

The composition of Example 1, further comprising a pore volume between about 0.1 $cm^3/g$ and about 30 $cm^3/g$.

Example 11

The composition of Example 10, wherein the pore volume is between about 0.1 $cm^3/g$ and about 1.6 $cm^3/g$.

Example 12

The composition of Example 1, further comprising an acid site density between about 50 µmol acid sites/g composition (µmol/g) and about 350 µmol/g.

Example 13

The composition of Example 12, wherein the acid site density is between about 125 µmol/g and about 300 µmol/g.

Example 14

The composition of Example 1, further comprising a surface area between about 50 $m^2/g$ and about 500 $m^2/g$.

Example 15

The composition of Example 14, wherein the surface area is between about 140 $m^2/g$ and about 265 $m^2/g$.

Example 16

The composition of Example 1, further comprising a basic site density between about 1.0 µmol basic sites/g composition (µmol/g) and about 200 µmol/g.

Example 17

The composition of Example 16, wherein the basic site density is between about 25 µmol/g and about 150 µmol/g.

Example 18

A method comprising: contacting a feedstock comprising at least one of a biomass or a non-biomass carbonaceous material with a composition and supercritical methanol, wherein: the contacting converts at least a portion of the feedstock to a mixture comprising an alcohol, and the composition comprises: copper (Cu), aluminum (Al), oxygen, and an element (M) comprising at least one of magnesium, cerium, or a transition metal, wherein: the copper and the element are present at a first molar ratio relative to the aluminum between about 0.1:1 and about 30:1 ((Cu+M):Al), and the copper and the element are present at a second molar ratio between about 0.1:4 and about 20:1 (Cu:M).

Example 19

The method of Example 18, wherein: a yield of the alcohol is between about 40 wt % and about 99 wt %, and the yield is based on the carbon content of the biomass.

Example 20

The method of Example 18, wherein the feedstock is solvolyzed in the methanol.

Example 21

The method of Example 18, wherein the contacting is performed at a temperature between about 200° C. and about 350° C.

Example 22

The method of Example 18, wherein the contacting is performed at a pressure between about 1200 psig and about 4000 psig.

Example 23

The method of Example 18, wherein the contacting is performed for a time period between about 2 hours and 8 hours.

Example 24

The method of Example 18, wherein the contacting is performed in a batch reactor.

Example 25

The method of Example 18, wherein the contacting is performed at a ratio of the composition to the feedstock between about 1:1 and about 0.01:1.0.

Example 26

The method of Example 18, wherein the contacting is performed in a flow reactor.

Example 27

The method of Example 18, wherein: the feedstock is solvolyzed in the methanol to form a solution, and the solution to composition weight hour space velocity is between about 0.01 $h^{-1}$ and about 10 $h^{-1}$.

Example 28

The method of Example 18, wherein the alcohol has between two and six carbon atoms.

Example 29

The method of Example 18, wherein the alcohol comprises at least one of 2-methyl-1-propanol, ethanol, 1-propanol, 2-propanol, 2-butanol, iso-butanol, 1-butanol, 3-methyl-2-butanol, 2-methyl-2-pentanol, 1-pentanol, or 3-hexanol.

Example 30

The method of Example 29, wherein the mixture further comprises at least one of methyl acetate, 2-methyl furan, methyl propionate, methyl butyrate, 3-hexanone, 2-methyl (methyl butanoate), 1,2-butanediol, methyl pentanoate, or 2-methylcyclopentanone.

Example 31

A fuel composition comprising at least one of 2-methyl-1-propanol, ethanol, 1-propanol, 2-propanol, 2-butanol, iso-butanol, 1-butanol, 3-methyl-2-butanol, 2-methyl-2-pentanol, 1-pentanol, or 3-hexanol.

Example 32

The fuel composition of Example 31, further comprising at least one of methyl acetate, 2-methyl furan, methyl propionate, methyl butyrate, 3-hexanone, 2-methyl(methyl butanoate), 1,2-butanediol, methyl pentanoate, or 2-methylcyclopentanone.

Example 33

The fuel composition of Example 31, further comprising a lower heat value between about 38 MJ/kg and about 44 MJ/kg.

Example 34

The fuel composition of Example 31, further comprising a density at 15° C. between about 0.74 g/mL and about 0.78 g/mL.

Example 35

The fuel composition of Example 31, further comprising a research octane number between about 85 and about 95.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
   copper (Cu), aluminum (Al), oxygen, and cerium (Ce); and
   an average pore size between about 0.1 nm and about 60 nm, wherein:
   the copper and the cerium are present at a first molar ratio relative to the aluminum between about 0.1:1 and about 30:1 ((Cu+Ce):Al),
   the copper and the cerium are present at a second molar ratio between about 0.1:4 and about 20:1 (Cu:Ce), and
   each of the copper, aluminum, and cerium are covalently incorporated into an oxide.

2. The composition of claim 1, wherein the second molar ratio is between about 1:1 and about 10:4 (Cu:Ce).

3. The composition of claim 1, further comprising a third molar ratio of a molar hydrogen ($H_2$) capacity, in moles of $H_2$ per gram of the composition ($c_1$), to a molar concentration of the Cu, in moles of Cu per gram of the composition ($c_2$), wherein the third molar ratio is between about 0.5:1 and about 10:1 ($c_1$:$c_2$).

4. The composition of claim 3, wherein the third molar ratio is between about 1:1 and about 3.4:1.

5. The composition of claim 1, wherein the average pore size is between about 1.0 nm and about 10 nm.

6. The composition of claim 1, further comprising a pore volume between about 0.1 cm$^3$/g and about 30 cm$^3$/g.

7. The composition of claim 6, wherein the pore volume is between about 0.1 cm$^3$/g and about 1.6 cm$^3$/g.

8. The composition of claim 1, further comprising an acid site density between about 50 μmol acid sites/g composition (μmol/g) and about 350 μmol/g.

9. The composition of claim 8, wherein the acid site density is between about 125 μmol/g and about 300 μmol/g.

10. The composition of claim 1, further comprising a surface area between about 50 m$^2$/g and about 500 m$^2$/g.

11. The composition of claim 10, wherein the surface area is between about 140 m$^2$/g and about 265 m$^2$/g.

12. The composition of claim 1, further comprising a basic site density between about 1.0 μmol basic sites/g composition (μmol/g) and about 200 μmol/g.

13. The composition of claim 12, wherein the basic site density is between about 25 μmol/g and about 150 μmol/g.

14. A method comprising:
contacting a feedstock comprising at least one of a biomass or a non-biomass carbonaceous material with a composition and supercritical methanol, wherein:
the contacting converts at least a portion of the feedstock to a mixture comprising an alcohol, and
the composition comprises:
copper (Cu), aluminum (Al), oxygen, and cerium (Ce); and
an average pore size between about 0.1 nm and about 60 nm, wherein:
the copper and the cerium are present at a first molar ratio relative to the aluminum between about 0.1:1 and about 30:1 ((Cu+Ce):Al),
the copper and the cerium are present at a second molar ratio between about 0.1:4 and about 20:1 (Cu:Ce), and
each of the copper, aluminum, and cerium are covalently incorporated into an oxide.

15. The method of claim 14, wherein the contacting is performed at a ratio of the composition to the feedstock between about 1:1 and about 0.01:1.0.

16. The method of claim 14, wherein the feedstock is solvolyzed in the methanol.

17. The method of claim 14, wherein the contacting is performed at a temperature between about 200° C. and about 350° C.

18. The method of claim 14, wherein the contacting is performed at a pressure between about 1200 psig and about 4000 psig.

19. The method of claim 14, wherein the contacting is performed for a time period between about 2 hours and 8 hours.

* * * * *